US012758085B2

(12) United States Patent
Wales et al.

(10) Patent No.: US 12,758,085 B2
(45) Date of Patent: Oct. 13, 2026

(54) MULTI-ENDOSCOPE PLATFORM COUPLING

(71) Applicant: Boston Scientific Scimed, Inc., Maple Grove, MN (US)

(72) Inventors: Ryan V. Wales, Northborough, MA (US); Ryan Vincent William Pollock, Leominster, MA (US); Kurt Nicholas Robakiewicz, Upton, MA (US); Paul Smith, Smithfield, RI (US); Scott E. Brechbiel, Acton, MA (US); Laura Elizabeth Christakis, Framingham, MA (US); John B. Golden, Norton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 595 days.

(21) Appl. No.: 18/347,032

(22) Filed: Jul. 5, 2023

(65) Prior Publication Data

US 2024/0008719 A1 Jan. 11, 2024

Related U.S. Application Data

(60) Provisional application No. 63/358,831, filed on Jul. 6, 2022.

(51) Int. Cl.

| | |
|---|---|
| ***A61B 1/00*** | (2006.01) |
| *A61B 1/015* | (2006.01) |
| *A61B 1/12* | (2006.01) |

(52) U.S. Cl.

CPC ...... *A61B 1/00119* (2013.01); *A61B 1/00068* (2013.01); *A61B 1/00128* (2013.01); *A61B 1/015* (2013.01); *A61B 1/126* (2013.01)

(58) Field of Classification Search

CPC ... F16L 5/025; F16L 5/14; F16L 27/12; F16L 41/18; F16L 51/00; F16L 37/505; F16L 39/04; A61B 1/00128; A61B 1/00112; A61B 1/00121; A61B 1/00119

See application file for complete search history.

(56) References Cited

U.S. PATENT DOCUMENTS

| | | | | |
|---|---|---|---|---|
| 1,856,656 A * | 5/1932 | Robinson | F16L 39/00 | 285/63 |
| 2,465,025 A * | 3/1949 | Maltbie | B61G 5/08 | 285/27 |
| 5,772,259 A * | 6/1998 | Geary | F16L 27/12 | 285/302 |

(Continued)

*Primary Examiner* — David Bochna

(74) *Attorney, Agent, or Firm* — Seager, Tufte & Wickhem, LLP

(57) ABSTRACT

Methods and systems for coupling a tube set to an endoscope. An illustrative adaptor for coupling a tube set to an endoscope may include a planar head portion having at least one aperture, at least one floating cylinder extending from a proximal end at least partially disposed within the at least one aperture of the planar head portion to a distal tip and having a first lumen extending therethrough, at least one O-ring positioned at the distal tip of the at least one floating cylinder, and at least one biasing element disposed about an outer surface of the at least one floating cylinder and extending from a first end adjacent the at least one aperture of the planar head portion to a second end proximal to the distal tip of the at least one floating cylinder.

15 Claims, 18 Drawing Sheets

(56) References Cited

U.S. PATENT DOCUMENTS

| | | | | |
|---|---|---|---|---|
| 11,571,114 | B2 * | 2/2023 | Shin | A61B 1/00112 |
| 11,576,566 | B2 | 2/2023 | Pollock et al. | |
| 11,826,022 | B2 * | 11/2023 | Shin | A61B 1/00121 |
| 2020/0400241 | A1 | 12/2020 | Stirnweiss et al. | |
| 2021/0177242 | A1 | 6/2021 | Remus | |
| 2021/0378487 | A1 | 12/2021 | Lagow et al. | |
| 2022/0192479 | A1 | 6/2022 | Harris et al. | |
| 2025/0352045 | A1 * | 11/2025 | Szychowski | A61B 1/00119 |

* cited by examiner

MULTI-ENDOSCOPE PLATFORM COUPLING

CROSS-REFERENCE TO RELATED APPLICATIONS

This application claims the benefit of U.S. Prov. Pat. App. No. 63/358,831, filed Jul. 6, 2022, titled MULTI-ENDOSCOPE PLATFORM COUPLING, which is incorporated herein by reference.

FIELD

This disclosure relates generally to medical device coupling assemblies and methods, and particularly to coupling mechanisms to supply fluid and/or gas to an endoscope.

BACKGROUND

Conventionally, endoscope devices have been widely used for performing diagnostic and/or therapeutic treatments. Endoscope devices are often coupled to additional devices, such as, but not limited to, processors, light sources, water sources, gas sources, etc. For example, water is supplied to the endoscope for irrigation and lens washing while air/gas is supplied for insufflation of the working lumen. As new endoscope technologies emerge, the new technologies may not be backwards compatible with older technology. This may necessitate more than one connector or types of connector be available for coupling the additional devices to the endoscope. However, having multiple pieces of tubing, hoses, couplers, etc. can be cumbersome within the procedure suite.

It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, an adaptor arranged and configured to couple a tube set to an endoscope may comprise a planar head portion having a first aperture and a second aperture, the first and second apertures extending through a thickness of the planar head portion, a first floating cylinder extending from a proximal end at least partially disposed within the first aperture of the planar head portion to a distal tip and having a first lumen extending therethrough, a first o-ring positioned at the distal tip of the first floating cylinder, a first biasing element disposed about an outer surface of the first floating cylinder and extending from a first end adjacent the first aperture of the planar head portion to a second end proximal to the distal tip of the first floating cylinder, a second floating cylinder extending from a proximal end at least partially disposed within the second aperture of the planar head portion adjacent the planar head portion to a distal tip and having a second lumen extending therethrough, a second o-ring positioned at the distal tip of the second floating cylinder, and a second biasing element disposed about an outer surface of the second floating cylinder and extending from a first end adjacent the second aperture of the planar head portion to a second end proximal to the distal tip of the first floating cylinder.

Alternatively or additionally to any of the examples above, in another example, the first end of the first biasing element may be configured to contact a lower surface of the planar head portion adjacent to or within the first aperture thereof and the first end of the second biasing element may be configured to contact a lower surface of the planar head portion adjacent to or within the second aperture thereof.

Alternatively or additionally to any of the examples above, in another example, the first biasing element may exert a distal force on the first floating cylinder.

Alternatively or additionally to any of the examples above, in another example, the second biasing element may exert a distal force on the second floating cylinder.

Alternatively or additionally to any of the examples above, in another example, the adaptor may further comprise a first ledge extending radially from an outer surface of the first floating cylinder.

Alternatively or additionally to any of the examples above, in another example, the adaptor may further comprise a second ledge extending radially from an outer surface of the second floating cylinder.

Alternatively or additionally to any of the examples above, in another example, the second end of the first biasing element may abut the first ledge.

Alternatively or additionally to any of the examples above, in another example, the first ledge may be proximal to the distal tip of the first floating cylinder.

Alternatively or additionally to any of the examples above, in another example, the second end of the second biasing element may abut the second ledge.

Alternatively or additionally to any of the examples above, in another example, the second ledge may be proximal to the distal tip of the second floating cylinder.

Alternatively or additionally to any of the examples above, in another example, the first and second ledges may extend about an entire circumference of the first and second floating cylinders.

Alternatively or additionally to any of the examples above, in another example, the first and second ledges may extend about less than an entire perimeter of the first and second floating cylinders.

Alternatively or additionally to any of the examples above, in another example, the first and second lumens may be configured to align with first and second openings in a female connector of an endoscope.

Alternatively or additionally to any of the examples above, in another example, the first lumen may be configured to receive a post defining a first opening of a male connector and the second lumen may be configured to align with a second opening of a male connector.

Alternatively or additionally to any of the examples above, in another example, the proximal ends of the first and second floating cylinders may be configured to be coupled with a tube set for use with an endoscopic system and the distal ends of the first and second floating cylinders may be configured to be coupled with an air/water connector on an endoscope.

In another example, an adaptor arranged and configured to couple a tube set to an endoscope may comprise a first inlet having a first coupling configuration and fluidly coupled to a first inlet tube, a second inlet having a second coupling configuration different from the first coupling configuration and fluidly coupled to a second inlet tube, a first outlet having a third coupling configuration and fluidly coupled to a first outlet tube, a second outlet having a fourth coupling configuration different from the third coupling configuration and fluidly coupled to a second outlet tube, an intermediate tube extending between and fluidly connecting the first and second inlet tubes with the first and second outlet tubes, a first flow selector positioned adjacent to an intersection of the first and second inlet tubes, and a second flow selector positioned adjacent to an intersection of the first and second outlet tubes.

Alternatively or additionally to any of the examples above, in another example, the first flow selector may be actuatable to selectively couple one of the first or second inlet tubes with the intermediate tube.

Alternatively or additionally to any of the examples above, in another example, the second flow selector may be actuatable to selectively couple one of the first or second outlet tubes with the intermediate tube.

Alternatively or additionally to any of the examples above, in another example, the first and second flow selectors may be actuatable to select a flow path between the first and second inlets and the first and second outlets.

Alternatively or additionally to any of the examples above, in another example, the third coupling configuration may be the same as the first coupling configuration and the fourth coupling configuration may be the same as the second coupling configuration.

In another example, an adaptor arranged and configured to couple a tube set to an endoscope may comprise a first outlet having a first coupling configuration, a second outlet having a second coupling configuration different from the first coupling configuration, a first inlet, and a flow selector in fluid communication with the first inlet. The flow selector may be operable to selectively fluidly couple the first inlet with the first or second outlet.

In another example, an adaptor arranged and configured to couple a tube set to an endoscope may comprise an outer shell, a deformable inner member disposed radially inward of the outer shell, the deformable inner member including a generally concave distal end surface and a tubular shaft defining a first lumen and extending distally from a central region of the distal end surface, and a plurality of lumens extending through the deformable inner member, the plurality of lumens surrounding the first lumen.

In another example, an adaptor arranged and configured to couple a tube set to an endoscope may comprise a first inlet having a first coupling configuration, a first outlet having a second coupling configuration different from the first coupling configuration, the first outlet in fluid communication with the first inlet, a second inlet having a third coupling configuration different from the first and second coupling configurations, and a second outlet having a fourth coupling configuration different from the first, second, and third coupling configurations, the second outlet in fluid communication with the second inlet.

In another example, an adaptor arranged and configured to couple a tube set to an endoscope may comprise a first outlet having a first coupling configuration, a second outlet having a second coupling configuration different from the first coupling configuration, a first inlet, and a rotating lock ring in fluid communication with the first inlet. The rotating lock ring may be rotatable to selectively fluidly couple the first inlet with the first or second outlet.

In another example, an adaptor arranged and configured to couple a tube set to an endoscope may comprise a housing portion configured to engage a connector, a neck portion, an actuatable tube disposed within the neck portion, and a slide actuator. The slide actuator may be configured to move the move the actuatable tube along a longitudinal axis of the neck portion to selectively couple the actuatable tube with a female connector a male connector.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
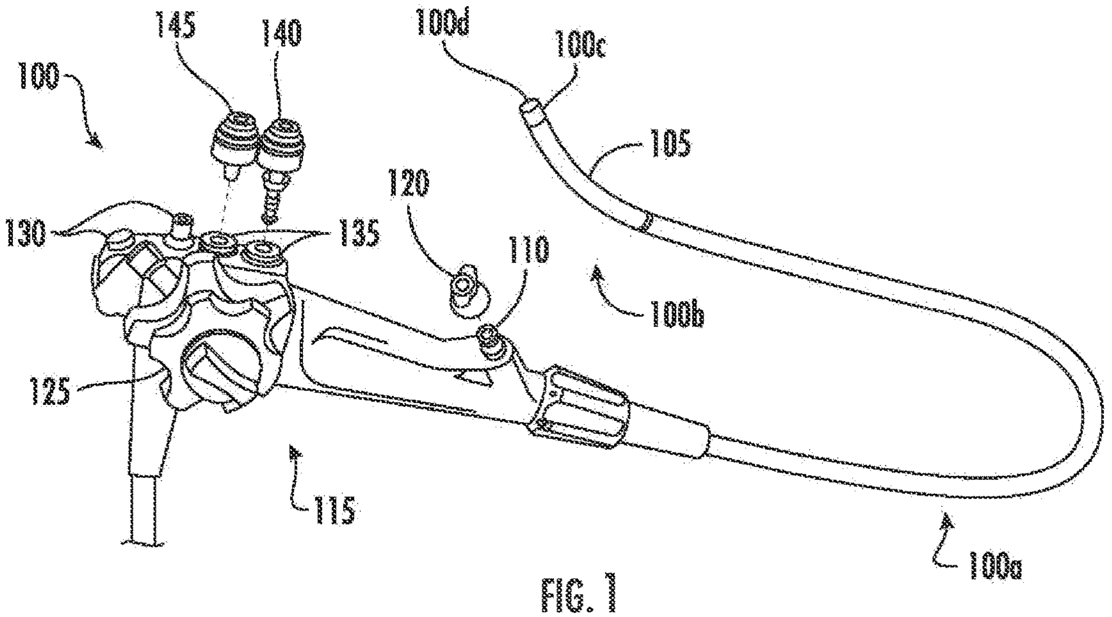
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Although embodiments of the present disclosure are described with specific reference to coupling a water and/or gas tubing to a connector portion of an endoscope, it should be appreciated that such embodiments may be used to couple various tubes in a variety of applications.

Although the present disclosure includes description of a manifold, bottle and tube set, couplers, and/or cap suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. Endoscope devices are often coupled to additional devices, such as, but not limited to, processors, light sources, water sources, gas sources, etc. For example, water is supplied to the endoscope for irrigation and lens washing while air/gas is supplied for insufflation of the working lumen. As new endoscope technologies emerge, the new technologies may not be backwards compatible with older technology. This may necessitate more than one connector or types of connector be available for coupling the additional devices to the endoscope. However, having multiple pieces of tubing, hoses, couplers, etc. can be cumbersome within the procedure suite. Disclosed herein are methods and systems for coupling fluid and gas lines across multiple endoscopic platforms with a single connector.

Figure 2:
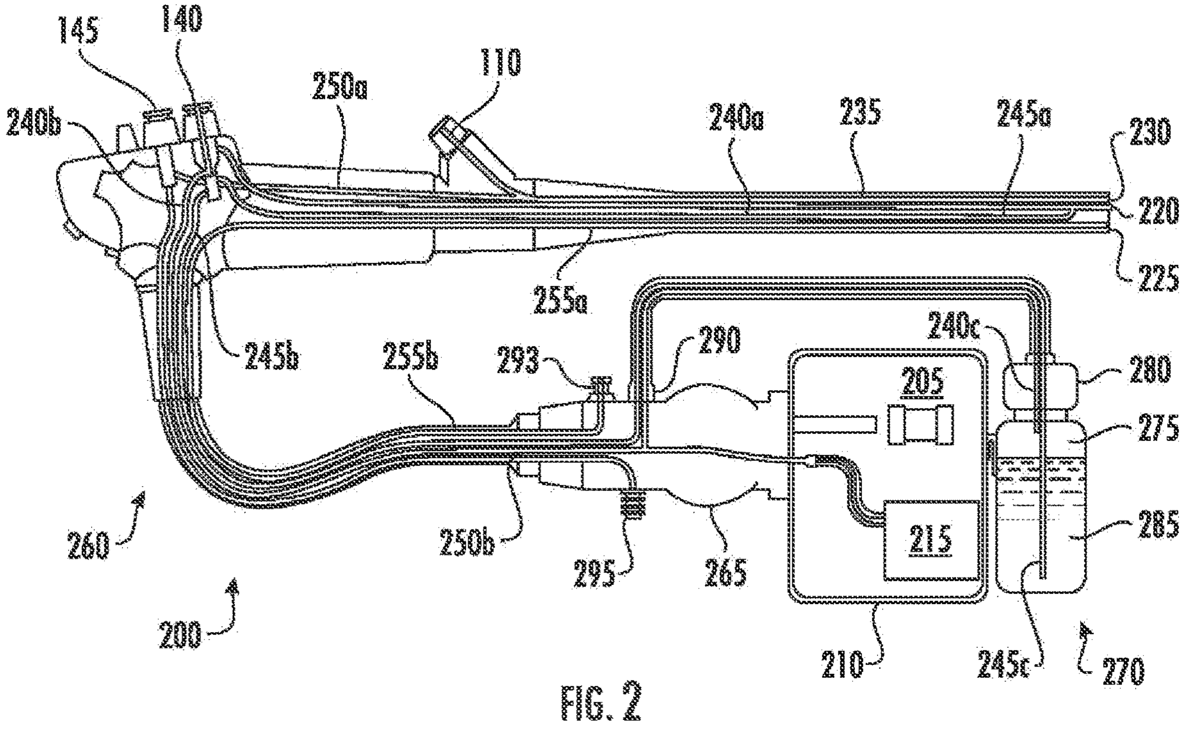
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100*a* that is inserted into a patient. A light source 205 feeds illumination light to a distal portion 100*b* of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100*a* may include a distal tip 100*c* provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 extends along the shaft 100*a* to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2). The other valve well 135 receives a suction valve 145 for operating a suction operation. A suction supply line 250*a* runs distally from the suction valve 145 along the shaft 100*a* to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) is fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240*c*. The gas feed line 240*b* from the umbilical 260 branches in the connector portion 265 to fluidly communicate with the gas supply tubing 240*c* at the detachable gas/lens wash connection 290, as well as the air pump 215. A length of lens wash tubing 245*c*, with one end positioned at the bottom of the reservoir 270, passes through the top 280 of the reservoir 270 to the same detachable connection 290 as the gas supply tubing 240*c* on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255*b* in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100. The detachable suction connection 295 may be detachable from the connector portion 265 and/or the suction feed line 250*b* and/or the vacuum source.

The gas feed line 240*b* and lens wash feed line 245*b* are fluidly connected to the valve well 135 for the gas/water valve 140 and configured such that operation of the gas/water valve in the well controls supply of gas or lens wash to the distal tip 100*c* of the endoscope 100. The suction feed line 250*b* is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240*b* in the umbilical 260, as well as through the gas supply tubing 240*c* to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240*a* and out the distal tip 100*c* of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash tubing 245*c*, through the connector portion 265, umbilical 260, through the gas/water valve 140 and down the lens wash supply line 245*a*, converging with the gas supply line 240*a* prior to exiting the distal tip 100*c* of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash tubing 245*c*, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240*c* to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255*b* in the umbilical 260 and the irrigation supply line 255*a* endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255*b* in the umbilical, and down the irrigation supply line in the shaft 100*a* of the endoscope to the distal tip 100*c*. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash tubing 245*c*, may be placed in the path of the irrigation supply tubing to help prevent back-flow into the reservoir after water has passed the valve. In some cases, irrigation water may be supplied from the water reservoir 270. Some illustrative systems where the supply tubing for irrigation and lens wash are connected to and drawn from a single water reservoir are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference.

In some cases, the type of receiver or coupling configuration for receiving the gas/lens wash connection 290 on the outside of the connector portion 265 may vary depending on the manufacturer and/or age of the connector portion 265. While the illustrative receivers are described with respect to the gas/lens wash connection 290 and/or its respective receiver or coupler on the connector portion, it should be understood the receivers and coupling configurations described herein may be used at other connection points, as desired. FIG. 3A depicts a perspective view of an illustrative receiver 300 that may be used as a gas/lens wash connection 290 and/or the receiver on the connector portion 265. Generally, the receiver 300 may be a female receiver configured to receive a connection, coupler, adaptor, etc. within a cavity thereof. In the illustrative embodiment, an adaptor is configured to couple with the receiver 300 to couple the gas supply tubing 240*c* and the lens wash tubing 245*c* with the gas feed line 240*b* and the lens wash feed line 245*b* within the connector portion 265.

The receiver 300 may have a generally cylindrical body 302 extending from a first open end 304 to a second generally closed end 306. The cylindrical body 302 may further define a cavity 308 extending from the open first end 304 towards the generally closed second end 306. The cavity 308 may be sized and shaped to receive a coupling mechanism or adaptor therein. The generally closed second end 306 may include one or more apertures 310*a*, 310*b* extending through an entire thickness of an end wall 312. In some cases, one or both of the apertures 310*a*, 310*b* may include an elongate tubular member (not explicitly shown) defining a lumen therethrough and extending from the second end 306 towards the first end 304, although this is not required. The apertures 310*a*, 310*b* may be sized and shaped to fluidly couple the gas supply tubing 240*c* and the lens wash tubing 245*c* with the gas feed line 240*b* and the lens wash feed line 245*b*, respectively, within the connector portion 265. The receiver 300 may further include a bayonet style locking feature configured to releasably secure the adaptor to the receiver 300. For example, the receiver 300 may include one or more generally "L" shaped slots 314*a*, 314*b* formed in sidewall 316 of the cylindrical body 302. The slots 314*a*, 314*b* are configured to receive a mating protrusion on the adaptor (not explicitly shown). In other embodiments, the receiver 300 may include one or more radially extending protrusions configured to be received in a mating slot. When the adaptor is coupled with the receiver 300, the lumens of the gas supply tubing 240*c* and the lens wash tubing 245*c* are fluidly coupled with the gas feed line 240*b* and the lens wash feed line 245*b*, respectively, within the connector portion 265.

Figure 3B:
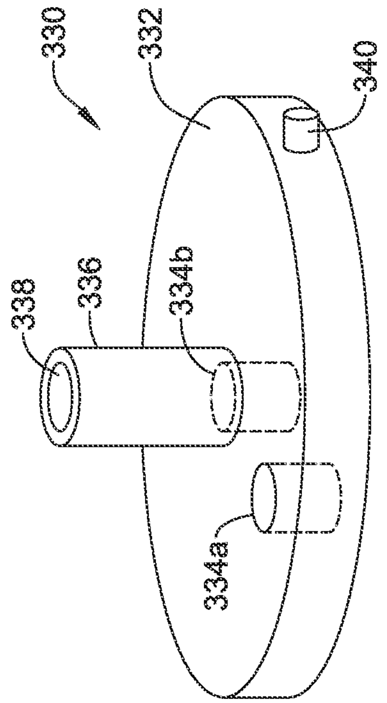
FIG. 3B depicts a perspective view of another illustrative receiver.
Figure 3A:
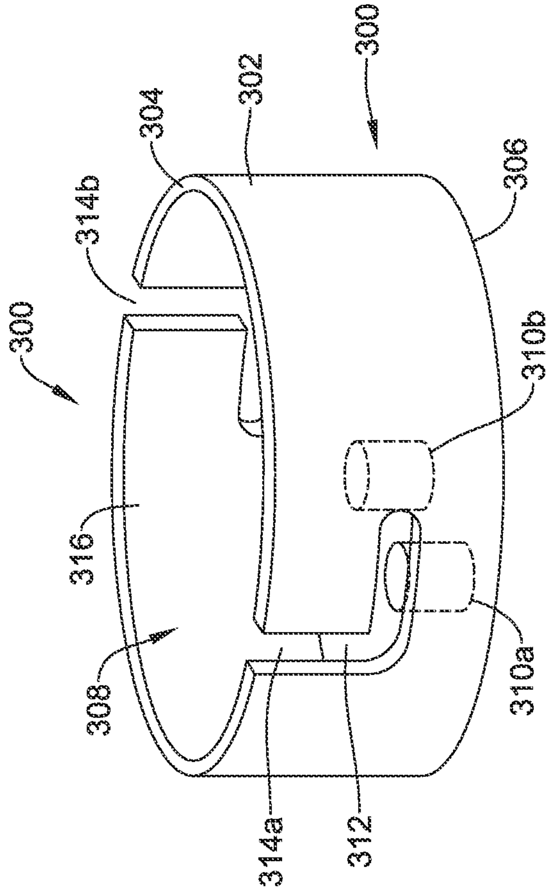
FIG. 3A depicts a perspective view of an illustrative receiver.

FIG. 3B depicts a perspective view of another illustrative receiver 330 that may be used as a gas/lens wash connection 290 and/or the receiver on the connector portion 265. Generally, the receiver 330 may be a male receiver configured to be at least partially received within a cavity of a connection, coupler, adaptor, etc. In the illustrative embodiment, an adaptor is configured to couple the gas supply tubing 240*c* and the lens wash tubing 245*c* with the gas feed line 240*b* and the lens wash feed line 245*b*, respectively, within the connector portion 265 via the receiver 330.

The receiver 330 may have a generally planar body 332. The receiver 330 may be sized and shaped to mate with a corresponding coupling mechanism or receiver. The generally planar body 332 may include one or more apertures 334*a*, 334*b* extending through an entire thickness of the planar body 332. In some cases, an elongate tubular member 336 defining a lumen 338 in fluid communication with an aperture 334*b* extends away from the generally planar body 332. While not explicitly shown, each aperture 334*a*, 334*b* may include an elongate tubular member. The apertures 334*a*, 334*b* may be sized and shaped to fluidly couple the gas supply tubing 240*c* and the lens wash tubing 245*c* with the gas feed line 240*b* and the lens wash feed line 245*b*, respectively, within the connector portion 265. When the adaptor is coupled with the receiver 330, the lumens of the of the gas supply tubing 240*c* and the lens wash tubing 245*c* are fluidly coupled with the gas feed line 240*b* and the lens wash feed line 245*b*, respectively, within the connector portion 265.

The receiver 330 may further include one or more protrusions 340 extending radially from a side of the planar body 332. The protrusion(s) 340 may be configured to be received within a mating slot on a mating adaptor or receiver. In other embodiments, the receiver 300 may include one or more generally "L" shaped slots configured to receive a mating protrusion. For example, the receiver 330 may be configured to be releasably coupled to the female receiver 300 of FIG. 3A. To couple the receivers 300, 330, the protrusions 340 of the male receiver 330 may be aligned with the slots 314*a*, 314*b* with the elongate tubular member 336 extending towards the second end 306 of the female receiver 300. The male receiver 330 may be longitudinally advanced until the protrusions 340 contacts the bend in the "L" shaped slot 314*a*, 314*b*. The male receiver 330 may then be rotated to secure the male receiver 330 to the female receiver 300. This may also bring the lumen 338 of the elongate tubular member 336 and the second aperture 334*b* of the male receiver 330 into fluid communication with the second aperture 310*b* of the female receiver 300 and may bring the first aperture 334*a* of the male receiver 330 into fluid communication with the first aperture 310*a* of the female receiver 300.

It can be seen that if the connector portion 265 of the endoscope 100 can have either a female receiver 300 or a male receiver 330, multiple tubing sets (e.g., having different receivers) may be required to be present in the procedure suite to ensure the tubing set can couple with the connector portion 265. This may cause confusion and logistical errors within the procedure suite (e.g., grabbed the wrong tube set, tube set won't couple to the connector, etc.). Alternative adaptors or receivers that can couple to either a female receiver 300 or a male receiver 330 may be desirable.

Figure 4B:
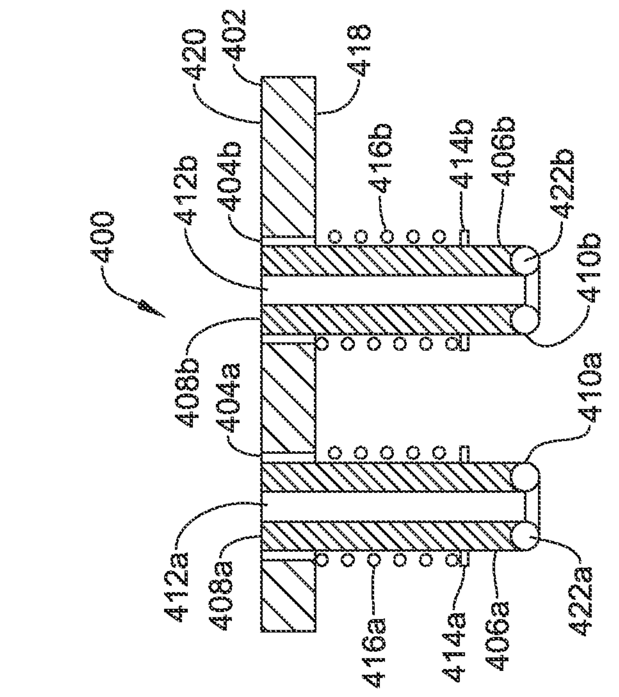
FIG. 4B depicts a cross-sectional view of the illustrative adaptor of FIG. 4A, taken at line 4B-4B.
Figure 4A:
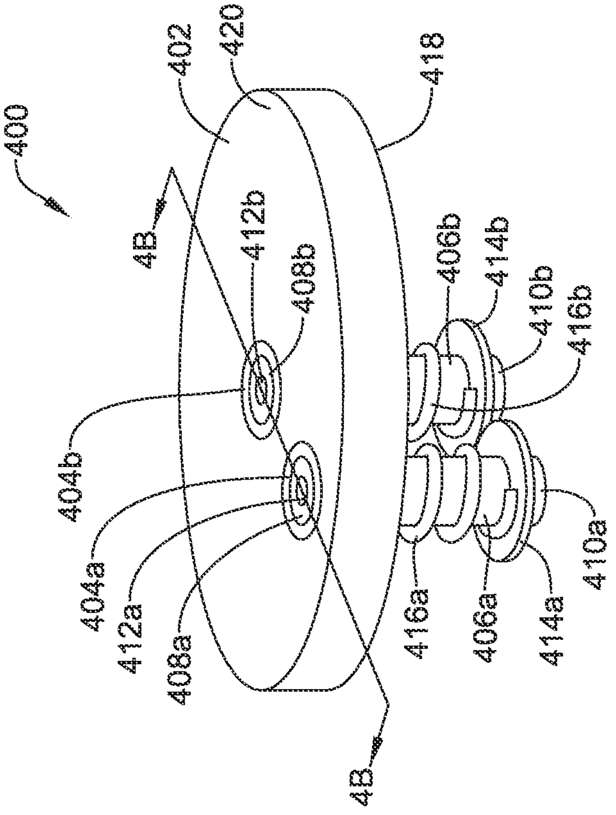
FIG. 4A depicts a perspective view of an illustrative adaptor that can couple to either a female receiver or a male receiver.

FIG. 4A is a perspective view of an illustrative adaptor 400 that can couple to either a female receiver 300 or a male receiver 330. FIG. 4B is a cross-sectional view of the illustrative adaptor 400 of FIG. 4A, taken at line 4B-4B. The adaptor 400 includes a planar head portion 402 having a first aperture 404*a* and a second aperture 404*b* extending through an entire thickness of the planar head portion 402. While the planar head portion 402 has a generally circular cross-sectional shape, it is contemplated that the planar head portion 402 may take other shapes, as desired.

The adaptor 400 further includes a first floating cylinder 406*a* and a second floating cylinder 406*b* freely movable within the apertures 404*a*, 404*b*. The floating cylinders 406*a*, 406*b* may float or be free from or have minimal contact with the walls of the apertures 404*a*, 404*b* to allow the floating cylinders 406*a*, 406*b* to move freely within the apertures 404*a*, 404*b*. The first floating cylinder 406*a* may be positioned at least partially within the first aperture 404*a*. In some cases, the first floating cylinder 406*a* may be coaxial with the first aperture 404*a*. The second floating cylinder 406*b* may be positioned at least partially within the second aperture 404*b*. In some cases, the second floating cylinder 406*b* may be coaxial with the second aperture 404*b*. Each of the floating cylinders 406*a*, 406*b* extends from a proximal end 408*a*, 408*b* adjacent to the planar head portion 402 to a distal tip 410*a*, 410*b*. Each of the floating cylinders 406*a*, 406*b* defines a lumen 412*a*, 412*b* extending from the proximal end 408*a*, 408*b* to the distal tip 410*a*, 410*b* thereof. The lumens 412*a*, 412*b* may have a diameter greater than a diameter of the elongate tubular member 336 on a male receiver 330 or the elongate tubular member of the female receiver 300, if so provided, such that the elongate tubular member 336 may be inserted into the lumen 412*a*, 412*b*. It is further contemplated that the lumens 412*a*, 412*b* may have a diameter greater than the first and second apertures 310*a*, 310*b* of the female receiver 300 or the first aperture 334*a* of the male receiver 330. Alternatively, the floating cylinders 406*a*, 406*b* may have an outer diameter that is less than an inner diameter of the elongate tubular members 336 such that the floating cylinders 406*a*, 406*b* is inserted into the lumen 338 of the elongate tubular members 336 and/or into the apertures 310*a*, 310*b*, 334*a*, 334*b* of the receivers 300, 330.

The floating cylinders 406*a*, 406*b* further include a rim or ledge 414*a*, 414*b* extending radially from an outer surface thereof. The ledges 414*a*, 414*b* may be positioned between the proximal end 408*a*, 408*b* and the distal tip 410*a*, 410*b*. For example, the ledges 414*a*, 414*b* may be positioned proximal to the distal tip 410*a*, 410*b*. The ledges 414*a*, 414*b* may extend about an entire perimeter of the floating cylinders 406*a*, 406*b* or less than an entire perimeter, as desired. A biasing element 416*a*, 416*b* is positioned between a lower surface 418 of the planar head portion 402 and the ledges 414*a*, 414*b* such that the biasing elements 416*a*, 416*b* abuts the lower surface 418 and the ledges 414*a*, 414*b*. The biasing element 416*a*, 416*b* may be configured to exert a distal biasing force on the floating cylinders 406*a*, 406*b* in a distal direction when the adaptor 400 is assembled with another receiver. In some embodiments, the biasing element 416*a*, 416*b* may be a helically wound spring. However, other structures configured to compress and resume an expanded shape to apply a force on the ledge 414*a*, 414*b* may be used as desired. In some embodiments, the biasing elements 416*a*, 416*b* may have a cross-sectional dimension that is greater than a diameter of the apertures 404*a*, 404*b*. This may prevent the biasing elements 416*a*, 416*b* from passing through or disengaging from the apertures. In some embodiments, a portion of the biasing elements 416*a*, 416*b* may be fixedly secured to the planar head portion 402, although this is not required. In some embodiments, for example, when the biasing element 416*a*, 416*b* is compressed, the proximal end 408*a*, 408*b* of the floating cylinders 406*a*, 406*b* may extend beyond an upper surface 420 of the planar head portion 402.

To assemble the adaptor 400 with tubes, such as, but not limited to, the gas feed supply 240*c* and the lens wash supply 245*c*, the ends of the tubes may be positioned within the apertures 404*a*, 404*b* such that the tube wall is disposed between an outer surface of the floating cylinders 406*a*, 406*b* and an inner surface of the apertures 404*a*, 404*b*. The ends of the tubes may form a friction fit with the apertures 404*a*, 404*b* and/or the floating cylinders 406*a*, 406*b* to secure the tubes to the adaptor 400. In some embodiments, the frictional force between the tubes and the floating cylinders 406*a*, 406*b* may secure the floating cylinders 406*a*, 406*b* relative to the planar head portion 402 while allowing the floating cylinders 406*a*, 406*b* to move along a longitudinal axis of the floating cylinders 406*a*, 406*b*. When the tubes are coupled to the floating cylinders 406*a*, 406*b*, the lumen of the tubes are in fluid communication with the lumens 412*a*, 412*b* of the floating cylinders 406*a*, 406*b*.

As shown in FIG. 4B, an O-ring 422*a*, 422*b* or other sealing member, is positioned adjacent each of the distal tips 410*a*, 410*b* of the floating cylinders 406*a*, 406*b*. In some cases, the O-rings 422*a*, 422*b* may be secured to the distal tips 410*a*, 410*b* using, for example, adhesives, friction fit, over molding, or other techniques. The O-rings 422*a*, 422*b* may be configured to provide a fluid tight seal between the adaptor 400 and the receiver to which it is coupled. In some cases, the O-rings 422*a*, 422*b* may be formed from a compressible material.

Figure 4C:
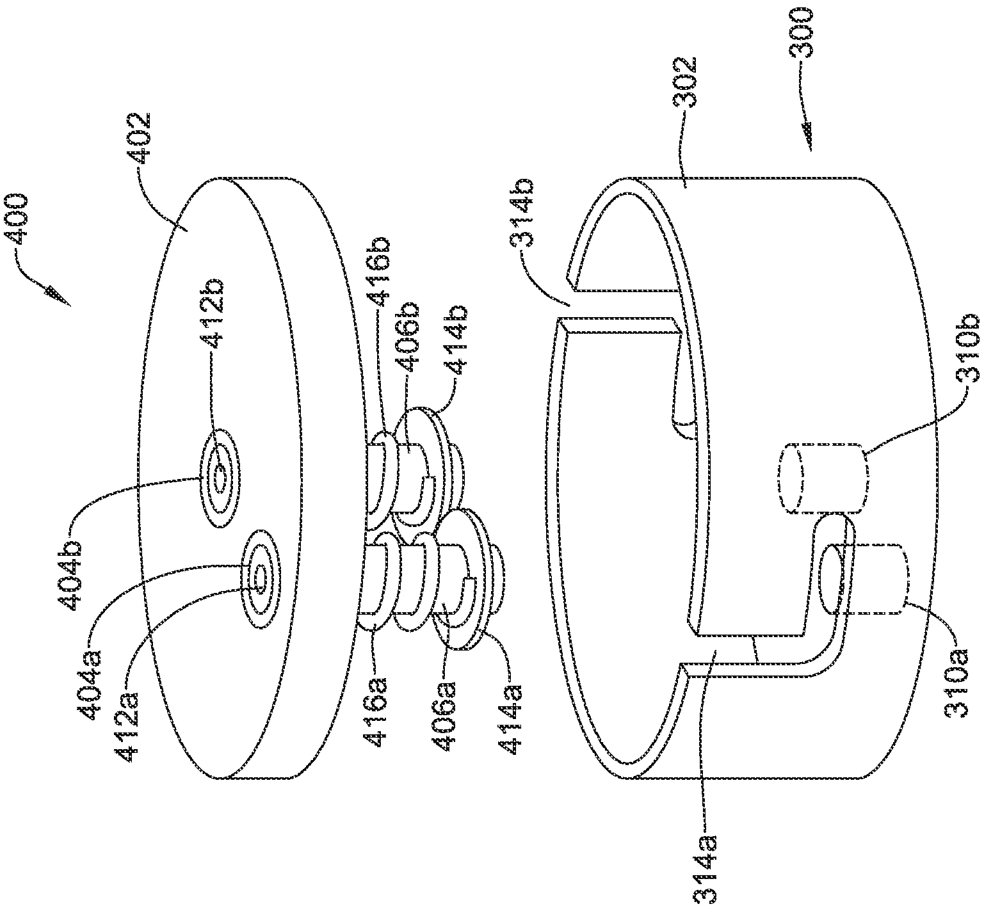
FIG. 4C depicts an exploded perspective view of the illustrative adaptor of FIG. 4A with a female receiver.

FIG. 4C is an exploded perspective view of an illustrative adaptor 400 with a female receiver 300. When assembled, the distal tips 410*a*, 410*b* of the floating cylinders 406*a*, 406*b* are configured to be fluidly and/or mechanically coupled with the female receiver 300 to couple the adaptor 400 (and thus the attached water/gas tubes) to the connector portion 265 of the endoscope system 200. To assemble the adaptor 400 with the receiver 300, the floating cylinders 406*a*, 406*b* are aligned with the apertures 310*a*, 310*b*. For example, the distal tip 410*a* of first floating cylinder 406*a* may be aligned with the first aperture 310*a* such that the first lumen 412*a* is in fluid communication with the first aperture 310*a*. Similarly, the distal tip 410*b* of the second floating cylinder 406*b* may be aligned with the second aperture 310*b* such that the second lumen 412*b* is in fluid communication with the second aperture 310*b*. In some cases, the planar head portion 402 may include a radially extending protrusion configured to engage the slots 314*a*, 314*b* to secure the adaptor 400 with the female receiver 300. In other cases, an outer surface of the planar head portion 402 of the adaptor 400 may frictionally engage an inner surface of the cylindrical body 302 of the female receiver 300. In yet other examples, a strap or other retention feature may be used to secure the adaptor 400 to the receiver 300. To ensure a fluid tight seal, the planar head portion 402 may compress the biasing elements 416*a*, 416*b* such that the biasing elements 416*a*, 416*b* are exerting a distal force on the ledges 414*a*, 414*b* to bias the O-rings 422*a*, 422*b* towards the apertures 310*a*, 310*b*. The pressure from the biasing elements 416*a*, 416*b* may push the O-rings 422*a*, 422*b* against the edge of the apertures 310*a*, 310*b* for a fluid tight seal. It is contemplated that if there is not a flow path to interface with the one of the lumens 412*a*, 412*b* (e.g., only one aperture 310*a*, 310*b* is present), the O-ring 422*a*, 422*b* may be pushed against the end wall 312 of the receiver 300 to prevent fluid from leaking out of the respective lumen 412*a*, 412*b*.

Figure 4D:
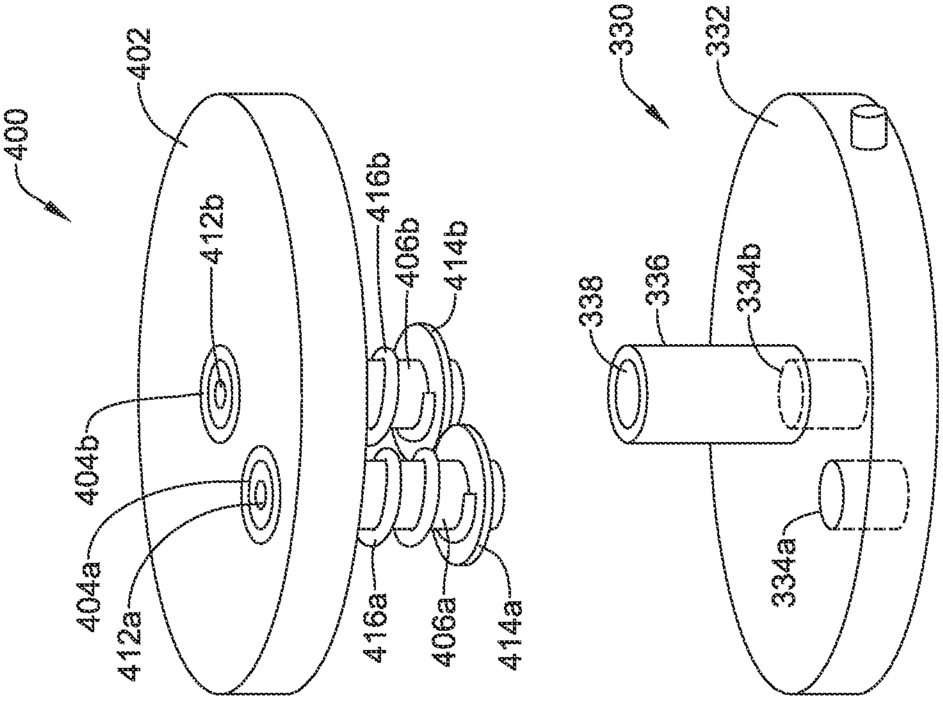
FIG. 4D depicts an exploded perspective view of the illustrative adaptor of FIG. 4A with a male receiver.

FIG. 4D is an exploded perspective view of an illustrative adaptor 400 with a male receiver 330. When assembled, the distal tips 410*a*, 410*b* of the floating cylinders 406*a*, 406*b* are configured to be fluidly and/or mechanically coupled with the male receiver 330 to couple the adaptor 400 (and thus the attached water/gas tubes) to the connector portion 265 of the endoscope system 200. To assemble the adaptor 400 with the receiver 330, the floating cylinders 406*a*, 406*b* are aligned with the apertures 334*a*, 334*b*. For example, the distal tip 410*a* of first floating cylinder 406*a* may be aligned with the first aperture 334*a* such that the first lumen 412*a* is in fluid communication with the first aperture 334*a*. The second floating cylinder 406*b* may be aligned with the second aperture 334*b* by either positioning the second floating cylinder 406*b* over the elongate tubular member 336 or positioning the second floating cylinder 406*b* within the lumen 338 of the elongate tubular member 336 such that the second lumen 412*b* is in fluid communication with the second aperture 334*b*. In some cases, the frictional engagement between the floating cylinders 406*a*, 406*b* and the elongate tubular member 336 and/or apertures 334*a*, 334*b* may secure the adaptor 400 to the male receiver 330. In yet other examples, a strap or other retention feature may be used to secure the adaptor 400 to the receiver 330. To ensure a fluid tight seal, the planar head portion 402 may compress the biasing elements 416*a*, 416*b* such that the biasing elements 416*a*, 416*b* are exerting a distal force on the ledges 414*a*, 414*b* to bias the O-rings 422*a*, 422*b* towards the apertures 334*a*, 334*b*. The pressure from the biasing elements 416*a*, 416*b* may push the O-rings 422*a*, 422*b* against the edge of the apertures 334*a*, 334*b* for a fluid tight seal. It is contemplated that if there is not a flow path to interface with the one of the lumens 412*a*, 412*b* (e.g., only one aperture 334*a*, 334*b* is present), the O-ring 422*a*, 422*b* may be pushed against the planar body 332 of the receiver 330 to prevent fluid from leaking out of the respective lumen 412*a*, 412*b*.

Figure 5A:
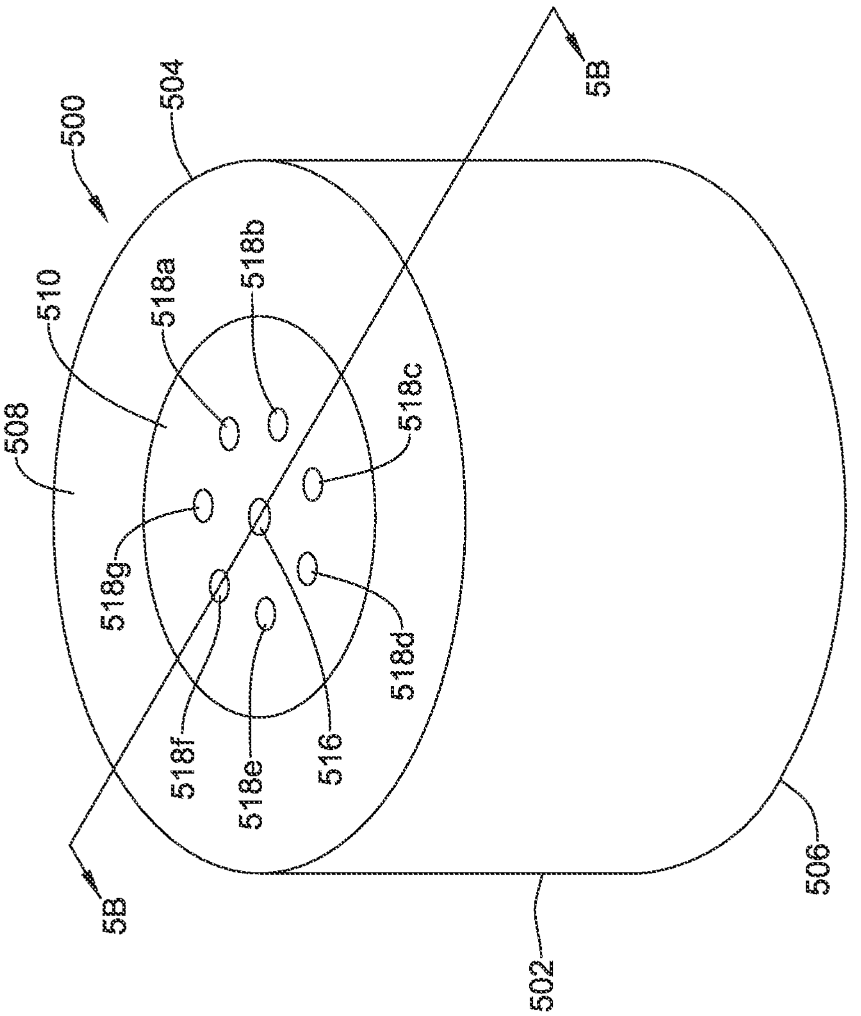
FIG. 5A depicts perspective view of another illustrative adaptor that can couple to either a female receiver or a male receiver.
Figure 5B:
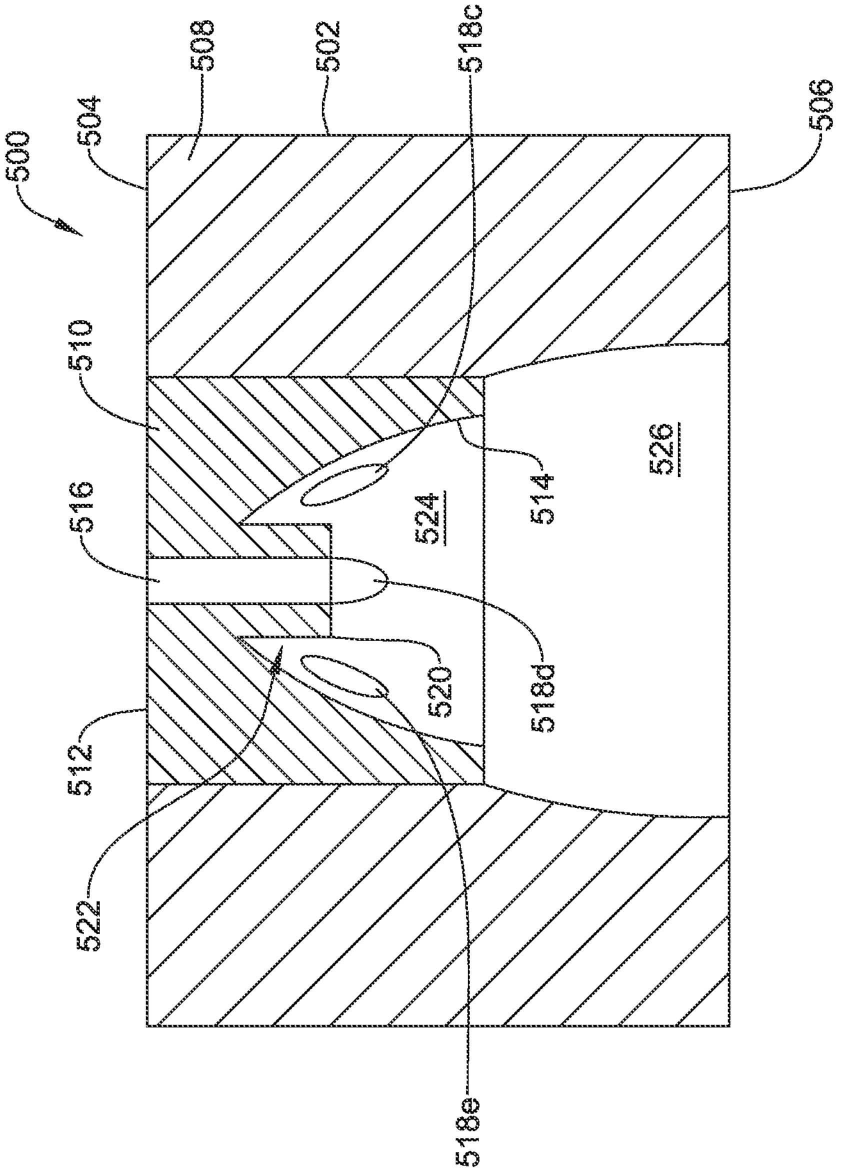
FIG. 5B depicts a cross-sectional view of the illustrative adaptor of FIG. taken at line 5B-5B.

FIG. 5A is a perspective view of another illustrative adaptor 500 that can couple to either a female receiver 300 or a male receiver 330. FIG. 5B is a cross-sectional view of the illustrative adaptor 500 of FIG. 5A, taken at line 5B-5B. The adaptor 500 includes an adaptor body 502 extending from a proximal end 504 to a distal end 506. The adaptor body 502 may include an outer shell 508 and a deformable inner member 510. The outer shell 508 may be formed from a rigid or semi-rigid material which allows a clinician to grip the adaptor 500 and/or to twist or press the adaptor 500 onto the receiver 300, 330. In some embodiments, the outer shell 508 may be omitted.

Referring additionally to FIG. 5B, the inner member 510 may have a generally flat or planar proximal end surface 512 and a generally concave distal end surface 514. A tubular shaft 520 may extend distally from a central region of the distal end surface 514. This is just an example. Other surface configurations may be used as desired. The inner member 510 may be formed from an extremely soft durometer rubber or polymer that can flex out of the way or around a receiver 300, 330. In some examples, the inner member 510 may be formed from soft silicones, urethanes, or other materials. The inner member 510 may be deformable such that when it is placed in contact with another member, the distal surface 514 takes the form of the other member. For example, if the distal surface 514 is positioned against a flat surface, the portion of the distal tip in contact with the flat surface will flatten to rest against the flat surface or move towards the surface. In some embodiments, a distal portion 522 of the tubular shaft 520 may be formed from a more rigid material than the concave distal surface 514. Thus, when the tubular shaft 520 contacts a surface, the concave distal surface 514 flexes upwards to allow fluid flow within a first chamber 524 of the adaptor 500.

The inner member 510 may include a first lumen 516 and a plurality of lumens 518*a*, 518*b*, 518*c*, 518*d*, 518*e*, 518*f*, 518*g* surrounding the first lumen 516. In some examples, the first lumen 516 may be centrally located with the plurality of lumens 518*a*, 518*b*, 518*c*, 518*d*, 518*e*, 518*f*, 518*g* arranged in an annular configuration or forming a concentric circle about the first lumen 516. While the plurality of lumens 518*a*, 518*b*, 518*c*, 518*d*, 518*e*, 518*f*, 518*g* is shown as including seven lumens, the plurality of lumens 518*a*, 518*b*, 518*c*, 518*d*, 518*e*, 518*f*, 518*g* may include more than seven or fewer than seven lumens, as desired. It is further contemplated that the lumens 516, 518*a*, 518*b*, 518*c*, 518*d*, 518*e*, 518*f*, 518*g* may be arranged in other configurations or patterns. The lumens 516, 518*a*, 518*b*, 518*c*, 518*d*, 518*e*, 518*f*, 518*g* may extend from the proximal end surface 512 to the distal end surface 514 to provide a fluid path through the inner member 510. In some examples, the first lumen 516 extends through the tubular shaft 520.

A lens wash supply 245*c* may be fluidly coupled to the first lumen 516 while a gas supply 240*c* may be fluidly coupled to one or more of the plurality of lumens 518*a*, 518*b*, 518*c*, 518*d*, 518*e*, 518*f*, 518*g* adjacent the proximal end 504 of the adaptor 504. It is contemplated that the lens wash supply 245*c* and/or gas supply 240*c* may be over molded with the adaptor 500. In another example, the lens wash supply 245*c* and/or gas supply 240*c* may be glued or otherwise adhered to the adaptor 500. When the adaptor 500 is assembled with a receiver 300, 330, the lens wash supply 245*c* is fluidly coupled to the connector portion 265 and the lens wash feed line 245*b*. For example, when the adaptor 500 is assembled with a receiver 300, 330 the tubular member 520 may be fluidly coupled with an aperture 310*b*, 338 (or other aperture) to connect the water line. When the adaptor 500 is assembled with a receiver, the gas supply 240*c* is fluidly coupled to the connector portion 265 and the gas feed line 240*b* via at least one of the lumens 518*a*, 518*b*, 518*c*, 518*d*, 518*e*, 518*f*, 518*g* and the first chamber 524. For example, when the adaptor 500 is assembled with a receiver 300, 330, the inner member 510 may create a fluid seal around the outer surface of the apertures 310*a*, 334*a* and air may flow through one or more of the lumens 518*a*, 518*b*, 518*c*, 518*d*, 518*e*, 518*f*, 518*g* and into aperture 310*a*, 334*a* via the first chamber 524.

In some embodiments, the inner member 510 may include a rigid ring that is inserted into the first chamber 524 or over molded into the membrane of the inner member 510. Thus, when the adaptor 500 is connected to a receiver 300, 330, the rigid ring may limit deformation of the inner member 510 and prevent the distal tip from sealing the air holes on the receiver 300, 330. For example, the rigid ring may prevent the distal surface 514 from contacting and sealing the air holes on the receiver 300, 330.

Figure 5C:
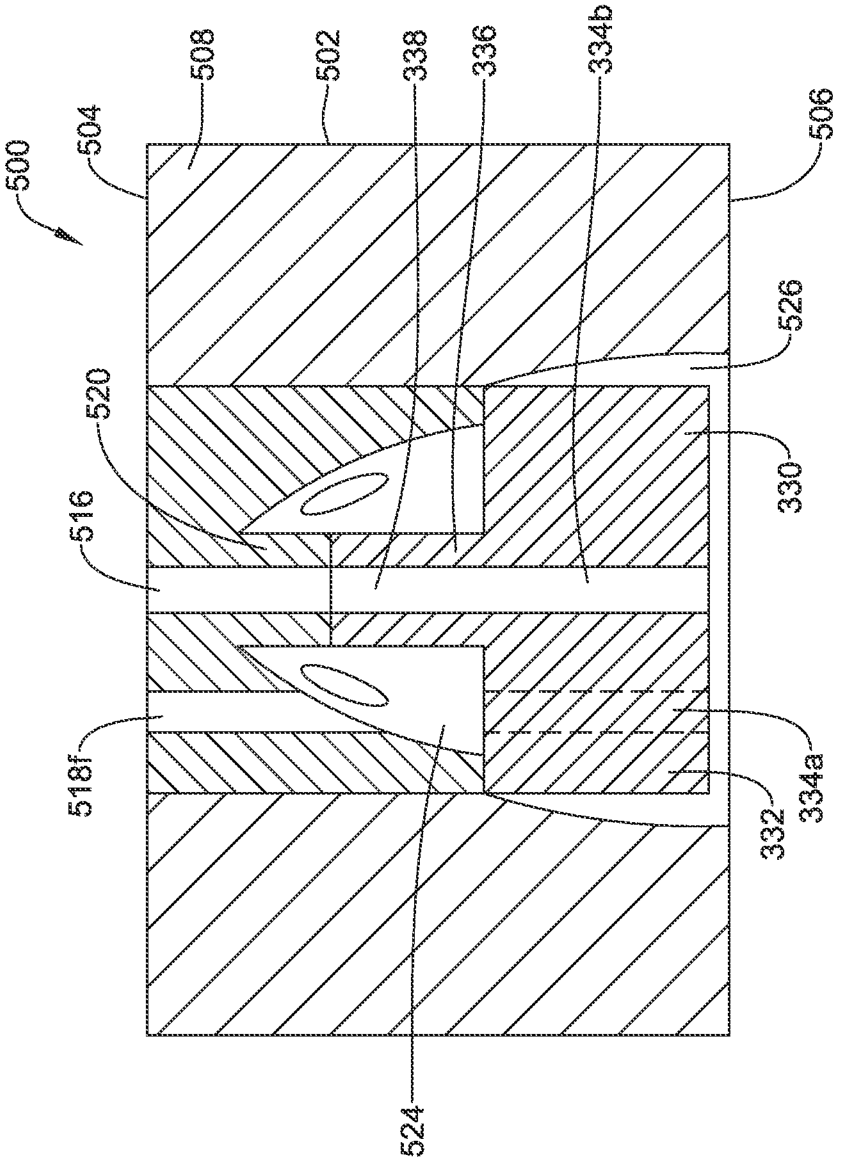
FIG. 5C depicts a cross-sectional view of the illustrative adaptor of FIG. coupled with a male receiver.

FIG. 5C is a cross-sectional view of the illustrative adaptor 500 assembled with a male receiver 330. As can be seen, the body 332 of male receiver 330 is received within a second cavity 526 of the adaptor 500. The elongate tubular member 338 extends into the first cavity 524 of the adaptor 500 and engages the tubular shaft 520 such that the first lumen 516 of the adaptor 500 is in fluid communication with the lumen 338 of the elongate tubular member 338 and the aperture 334*b*. The inner member 510 may deform about the receiver 330 to form a fluid tight seal between the tubular shaft 520 and the elongate tubular member 338 as well as between the body 332 and the distal surface 510. The first cavity 524 fluidly couples the plurality of lumens 518*a*, 518*b*, 518*c*, 518*d*, 518*e*, 518*f*, 518*g* and the aperture 334*a* of the receiver 330. While not explicitly shown, the adaptor 500 may mate with the apertures 310*a*, 310*b* of a female receiver 300 in a similar manner. In some cases, the distal surface 510 may be spaced from the second end 306 of the female receiver 300 by the rigid ring and/or the tubular member 520.

Figure 6:
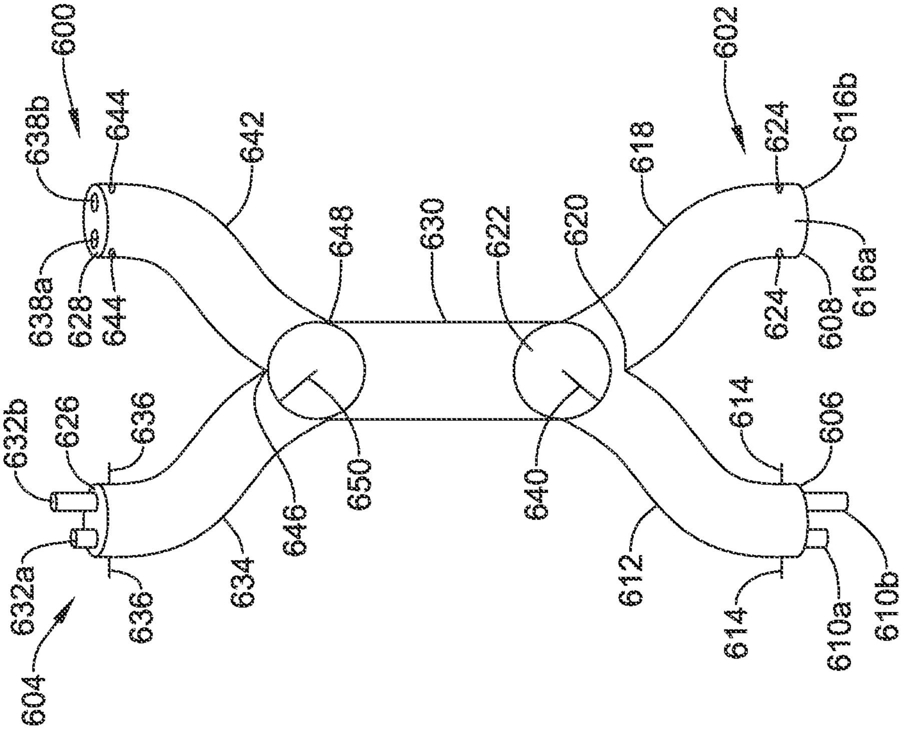
FIG. 6 depicts side view of another illustrative adaptor that can couple to either a female receiver or a male receiver.

FIG. 6 is a side view of another illustrative adaptor 600 that can couple to either a female receiver 300 or a male receiver 330. The adaptor 600 has a generally "X" shaped configuration and includes a first inlet end 602 and a second outlet end 604. The first inlet end 602 is configured to be coupled to a tube set including a gas supply 240*c* and a lens wash supply 245*c* and the second outlet end 604 is configured to be coupled to a connector 290 at the connector portion 265 to provide a fluid path from the reservoir 270 to the endoscope 100.

The first inlet end 602 includes a first inlet 606 having a first coupling configuration. In the illustrated embodiment, the first inlet 606 may have a male coupling configuration similar in form and function to the male receiver 330 described herein. For example, the first inlet 606 may include first and second elongate tubular members 610*a*, 610*b* configured to be coupled to a gas supply 240*c* and a lens wash supply 245*c*. The elongate tubular members 610*a*, 610*b* are each in fluid communication with separate fluid paths within a first inlet tube 612. The first inlet 606 may further include one or more radially extending protrusions 614 configured to engage a mating recess or opening in a female receiver.

The first inlet end 602 also includes a second inlet 608 having a second coupling configuration different from the first coupling configuration of the first inlet 606. In the illustrated embodiment, the second inlet 608 may have a female coupling configuration similar in form and function to the female receiver 300 described herein. For example, the second inlet 608 may include first and second openings 616*a*, 616*b* configured to be coupled to a gas supply 240*c* and a lens wash supply 245*c*. The openings 616*a*, 616*b* are each in fluid communication with separate fluid paths within a second inlet tube 618. The second inlet 608 may further include one or more "L" shaped openings or recesses 624 configured to engage a mating protrusion in a male receiver.

The first and second inlet tubes 612, 618 converge at an intersection 620. A first rotating dial or flow selector 622 configured to control a fluid flow path is positioned at the intersection 620. The flow selector 622 may be rotated to selectively fluidly couple the first or second inlet tubes 612, 618 with flow tubes in an intermediate tube 630. For example, if the first inlet 606 is coupled to the gas supply 240*c* and a lens wash supply 245*c*, the flow selector 622 is rotated to fluidly couple the fluid paths within the first inlet tube 612 with respective fluid paths in the intermediate tube 630 while blocking or isolating the fluid paths in the second inlet tube 618. The reverse configuration is also contemplated in which the flow selector 622 is rotated to fluidly couple the fluid paths within the second inlet tube 618 with respective fluid paths in the intermediate tube 630 while blocking or isolating the fluid paths in the first inlet tube 612. The flow selector 622 may include markings or other visual indicia 640 to indicate which flow path is connected to the intermediate tube 630.

The second outlet end 604 includes a first outlet 626 having a first coupling configuration. In the illustrated embodiment, the first outlet 626 may have a male coupling configuration similar in form and function to the male receiver 330 described herein. For example, the first outlet 626 may include first and second elongate tubular members 632*a*, 632*b* configured to be coupled to a connector 290 at a connector portion 265. The elongate tubular members 632*a*, 632*b* are each in fluid communication with separate fluid paths within a first outlet tube 634. The first outlet 626 may further include one or more radially extending protrusions 636 configured to engage a mating recess or opening in a female receiver.

The second outlet end 604 also includes a second outlet 628 having a second coupling configuration different from the first coupling configuration of the first outlet 626. In the illustrated embodiment, the second outlet 628 may have a female coupling configuration similar in form and function to the female receiver 300 described herein. For example, the second outlet 628 may include first and second openings 638*a*, 638*b* configured to be coupled to a connector 290 at a connector portion 265. The openings 638*a*, 638*b* are each in fluid communication with separate fluid paths within a second outlet tube 642. The second outlet 628 may further include one or more "L" shaped openings or recesses 644 configured to engage a mating protrusion in a male receiver.

The first and second outlet tubes 634, 642 converge at an intersection 646. A second rotating dial or flow selector 648 configured to control a fluid flow path is positioned at the intersection 646. The flow selector 648 may be rotated to selectively fluidly couple the intermediate tube 630 with the first or second outlet tubes 634, 642. For example, if the first outlet 626 is coupled to the connector 290 at the connector portion 265, the flow selector 648 is rotated to fluidly couple the fluid paths within the first outlet tube 634 with respective fluid paths in the intermediate tube 630 while blocking or isolating the fluid paths in the second outlet tube 642. The reverse configuration is also contemplated in which the flow selector 648 is rotated to fluidly couple the fluid paths within the second outlet tube 642 with respective fluid paths in the intermediate tube 630 while blocking or isolating the fluid paths in the first outlet tube 634. The flow selector 648 may include markings or other visual indicia 650 to indicate which flow path is connected to the intermediate tube 630.

The flow selectors 622, 648 may be rotated such that the first inlet 606 may be fluidly coupled with either the first outlet 626 or the second outlet 628 or the second inlet 608 may be fluidly coupled with either the first outlet 626 or the second outlet 628. This may allow a tube set having a male receiver to be coupled with a connector 290 that also has a male receiver and a tube set having a female receiver to be coupled with a connector 290 that also has a female receiver. It is contemplated the adaptor 600 may include more than two inlets 606, 608 and/or more than two outlets 626, 628 if additional endoscopes or bottle connectors are being used.

Figure 7A:
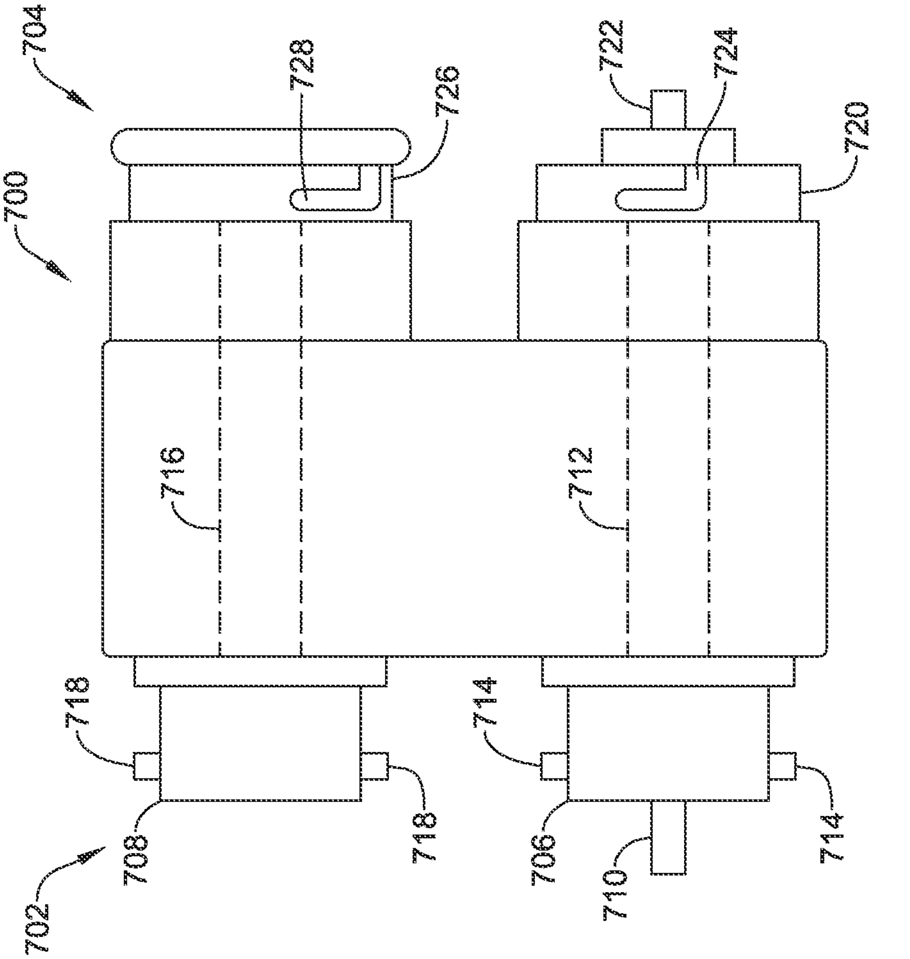
FIG. 7A depicts side view of another illustrative adaptor that can couple to either a female receiver or a male receiver.

FIG. 7A is a side view of another illustrative adaptor 700 that can couple to either a female receiver 300 or a male receiver 330. The adaptor 700 includes a first end 702 and a second end 704. The first end 702 includes a first inlet 706 having a first coupling configuration. In the illustrated embodiment, the first inlet 706 may have a male coupling configuration similar in form and function to the male receiver 330 described herein. For example, the first inlet 706 may include one or more elongate tubular members 710 configured to be coupled to a gas supply 240*c* and a lens wash supply 245*c*. The elongate tubular member(s) 710 are each in fluid communication with separate fluid paths within a first inlet tube 712. The first inlet 706 may further include one or more radially extending protrusions 714 configured to engage a mating recess or opening in a female receiver.

The first end 702 also includes a second inlet 708 having a second coupling configuration different from the first coupling configuration of the first inlet 706. In the illustrated embodiment, the second inlet 708 may have a female coupling configuration similar in form and function to the female receiver 300 described herein. For example, the second inlet 708 may include first and second openings (not explicitly shown) configured to be coupled to a gas supply 240*c* and a lens wash supply 245*c*. The openings are each in fluid communication with separate fluid paths within a second fluid tube 716. The second inlet 708 may further include one or more radially extending protrusions 718 configured to engage a mating recess or opening in a male receiver.

The second end 704 includes a first outlet 720 having a third coupling configuration. In the illustrated embodiment, the first outlet 720 may have a male coupling configuration similar in form and function to the male receiver 330 described herein. For example, the first outlet 720 may include one or more elongate tubular members 722 configured to be coupled to a connector 290 at a connector portion 265. The elongate tubular members 722 are each in fluid communication with separate fluid paths within the first fluid tube 712 to fluidly couple the first inlet 706 with the first outlet 720. The first outlet 720 may further include one or more "L" shaped openings or recesses 724 configured to engage a mating protrusion in a female receiver.

The second end 704 also includes a second outlet 726 having a fourth coupling configuration. In the illustrated embodiment, the second outlet 726 may have a female coupling configuration similar in form and function to the female receiver 300 described herein. For example, the second outlet 726 may include first and second openings (not explicitly shown) configured to be coupled to a connector 290 at a connector portion 265. The openings are each in fluid communication with separate fluid paths within the second fluid tube 716 to fluidly couple the second inlet 708 with the second outlet 726. The second outlet 726 may further include one or more "L" shaped openings or recesses 728 configured to engage a mating protrusion in a male receiver.

While the adaptor 700 has been described as having "inlets" and "outlets", the flow of fluid through the adaptor 700 may be reversed. For example, the gas supply 240*c* and the lens wash supply 245*c* may be coupled to the first or second outlets 720, 726 and the connector 290 may be connected to the first or second inlets 706, 708.

Figure 7B:
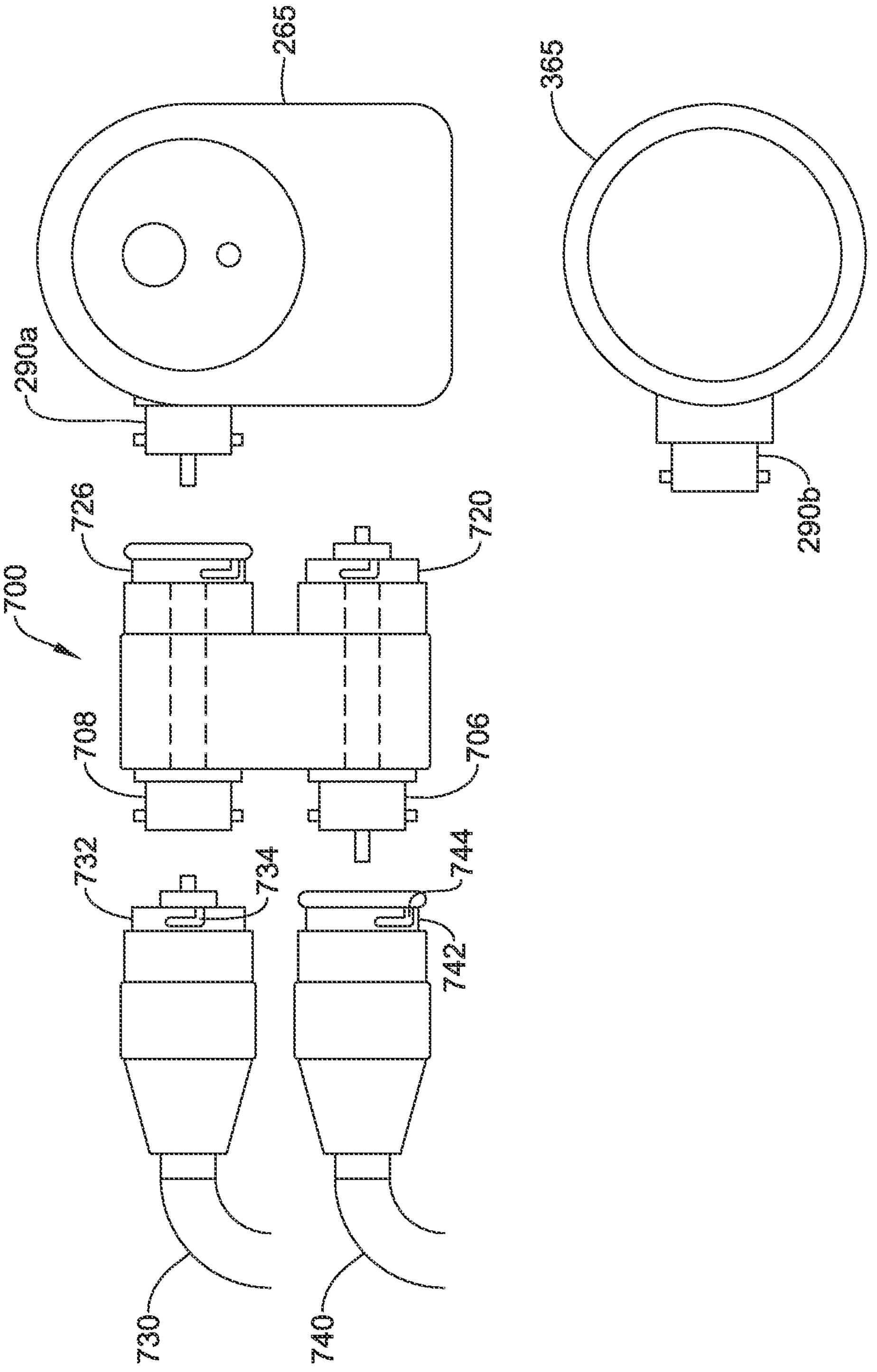
FIG. 7B depicts a side view of the illustrative adaptor of FIG. 7A with a first tube set, a second tube set, a connector portion having a first connector, and a connector portion having a second connector type.

Referring additionally to FIG. 7B which is a side view of the illustrative adaptor 700 with a first tube set 730, a second tube set 740, a connector portion 265 having a first connector 290*a*, and a connector portion 265 having a second connector type 290*b*. The first tube set 730 may include a gas supply 240*c* and a lens wash supply 245*c* therein. Further, the first tube set 730 may include a coupling 732 having a male configuration and a recess portion 734 of a bayonet style locking mechanism. The coupling 732 may be configured to mate directly with the second connector type 290*b*. To couple the coupling 732 with the first connector type 290*a*, the second inlet 708 of the adaptor 700 may be coupled to the coupling 732 and the second outlet 726 of the adaptor 700 coupled to the first connector type 290*a* to fluidly couple the gas supply 240*c* and the lens wash supply 245*c* with the connector portion 265 of the endoscope system 200.

The second tube set 740 may include a gas supply 240*c* and a lens wash supply 245*c* therein. Further, the second tube set 740 may include a coupling 742 having a female configuration and a recess portion 744 of a bayonet style locking mechanism. The coupling 742 may be configured to mate directly with the first connector type 290*a*. To couple the coupling 742 with the second connector type 290*b*, the first inlet 706 of the adaptor 700 may be coupled to the coupling 742 and the first outlet 720 of the adaptor 700 may be coupled to the second connector type 290*b* to fluidly couple the gas supply 240*c* and the lens wash supply 245*c* with the connector portion 265 of the endoscope system 200.

Figure 8A:
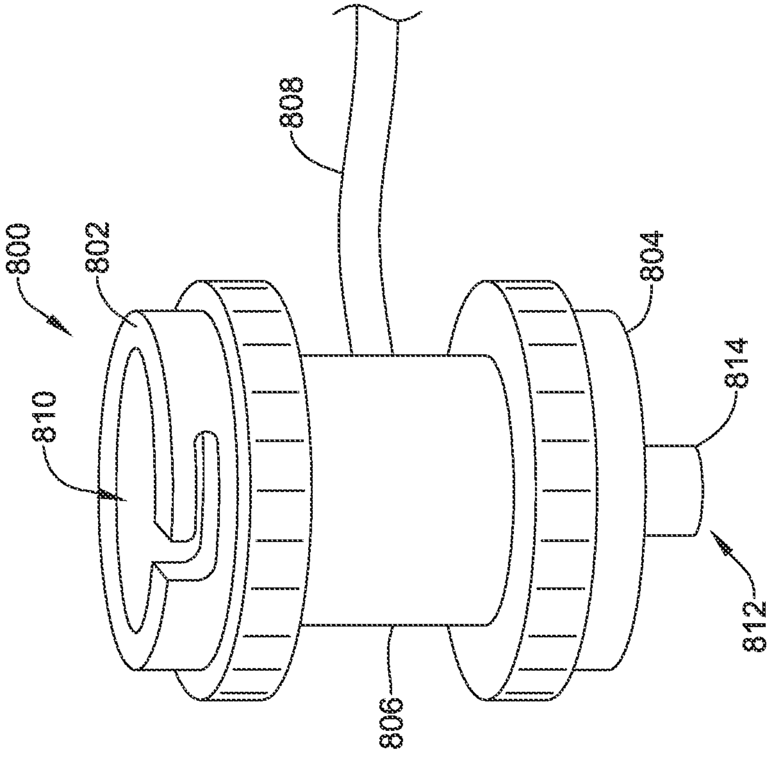
FIG. 8A depicts a side view of another illustrative adaptor that can couple to either a female receiver or a male receiver.

FIG. 8A is a side view of another illustrative adaptor 800 that can couple to either a female receiver 300 or a male receiver 330. The adaptor 800 extends from a first end 802 to a second end 804. A rotating lock ring 806 is positioned between the first end 802 and the second end 804. The rotating lock ring 806 is in fluid communication with a tube set 808 which may include a gas supply 240*c* and a lens wash supply 245*c* therein. The first end 802 of the adaptor 800 may include a first receiver 810 having a first coupling configuration. In the illustrated embodiment, the first receiver 810 may have a female coupling configuration similar in form and function to the female receiver 300 described herein. For example, the first receiver 810 may include first and second openings (not explicitly shown) configured to be coupled to a connector on the connector portion 265 of the endoscope system 200. The openings are each in selective fluid communication with separate fluid paths within the tube set 808. The first receiver 810 may further include one or more one or more "L" shaped openings or recesses 824 configured to engage a mating protrusion in a male receiver.

The second end 804 of the adaptor 800 may include a second receiver 812 having a first coupling configuration. In the illustrated embodiment, the second receiver 812 may have a male coupling configuration similar in form and function to the male receiver 330 described herein. For example, the second receiver 812 may include one or more elongate tubular members 814 configured to be coupled to a connector 290 at a connector portion 265 of the endoscope system 200. The openings are each in selective fluid communication with separate fluid paths within the tube set 808. The second receiver 812 may further include one or more one or more "L" shaped openings or recesses 822 (see, for example, FIG. 8C) configured to engage a mating protrusion in a male receiver.

The rotating lock ring 806 may be rotatable or movable to selectively couple the tube set 808 with either the first receiver 810 or the second receiver 812. For example, rotation of the rotating lock ring 806 may be translated into axial movement of an inner fluid path member 826 (see, for example, FIGS. 8B and 8C). In some embodiments, the axial translation of the inner fluid path member 826 may be caused by mating the adaptor 800 to the scope port. The inner fluid path member 826 of the adaptor 800 may be formed from an elastomeric material to provide sealing to the scope port. The rotating lock ring 806 may include markings or other visual indicia to provide an indication of the fluid flow path. The adaptor 800 may be used to couple the tube set 808 to an endoscope system 200 having either a male receiver or a female receiver.

Figure 8B:
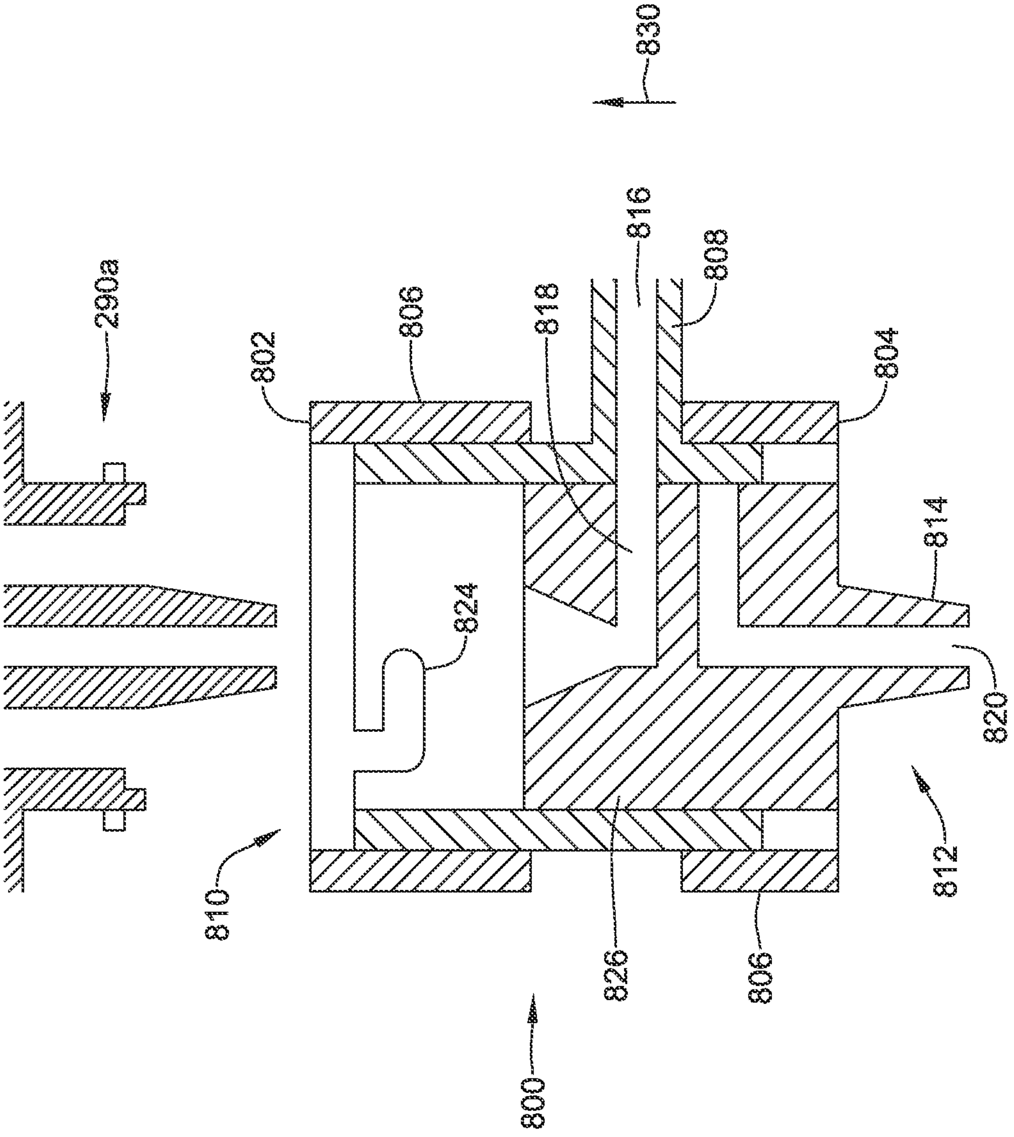
FIG. 8B depicts a schematic cross-sectional view of the illustrative adaptor with a first connector type.

FIG. 8B illustrates a schematic cross-sectional view of the illustrative adaptor 800 with a first connector type 290*a*. When the first connector type (e.g., a male receiver) 290*a* is present on the connector portion 265 of the endoscope system 200, the first receiver 810 of the adaptor 800 may be used to couple to the tube set 808 to the endoscope system 200. The rotating lock ring 806 is rotated to axially translate the inner fluid path member 826 in a direction generally indicated by arrow 830 such that the tube set lumens 816 align with the lumens 818 of the first receiver 810. The first receiver 810 is secured to the first connector type 290*a* with the bayonet style locking mechanism such that water/gas supply 245*c*, 240*c* and feed lines 245*b*, 240*b* are in fluid communication.

Figure 8C:
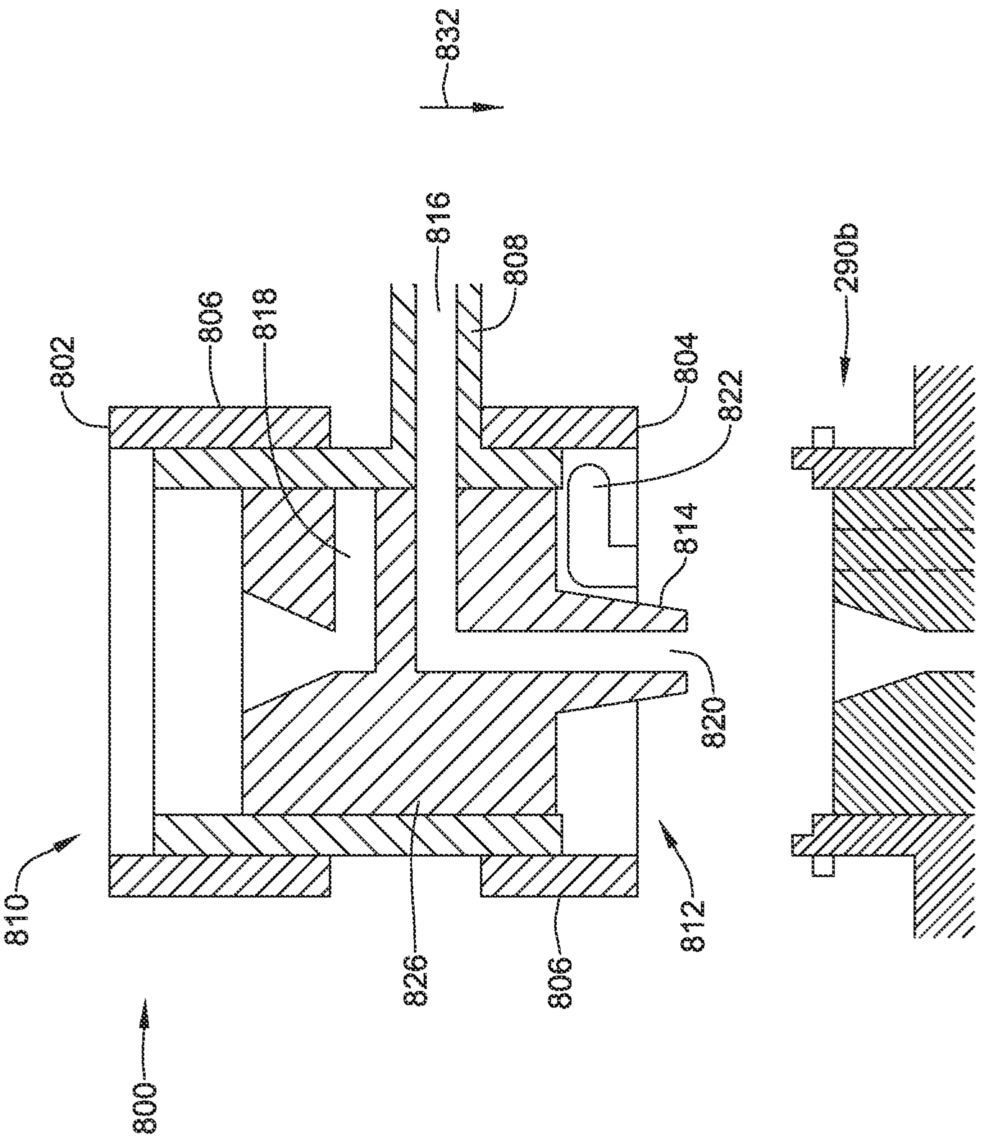
FIG. 8C depicts a schematic cross-sectional view of the illustrative adaptor with a first connector type.

FIG. 8C illustrates a schematic cross-sectional view of the illustrative adaptor 800 with second connector type 290*b*. When the second connector type (e.g., a female receiver) 290*b* is present on the connector portion 265 of the endoscope system 200, the second receiver 812 of the adaptor 800 may be used to couple to the tube set 808 to the endoscope system 200. The rotating lock ring 806 is rotated to axially translate the inner fluid path member 826 in a direction generally indicated by arrow 832 such that the tube set lumens 816 align with the lumens 820 of the second receiver 812. The second receiver 812 is secured to the second connector type 290*b* with the bayonet style locking mechanism such that water/gas supply 245*c*, 240*c* and feed lines 245*b*, 240*b* are in fluid communication.

Figure 9A:
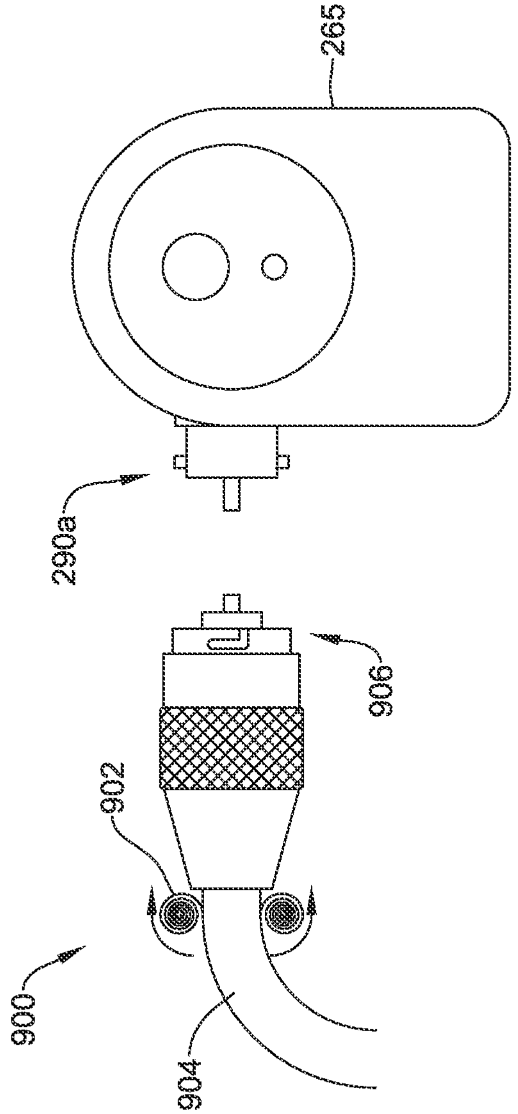
FIG. 9A depicts a side view of an illustrative coupling system for coupling a tube set having either a male or female connector to a connector portion having either a male or female connector in a first configuration.
Figure 9B:
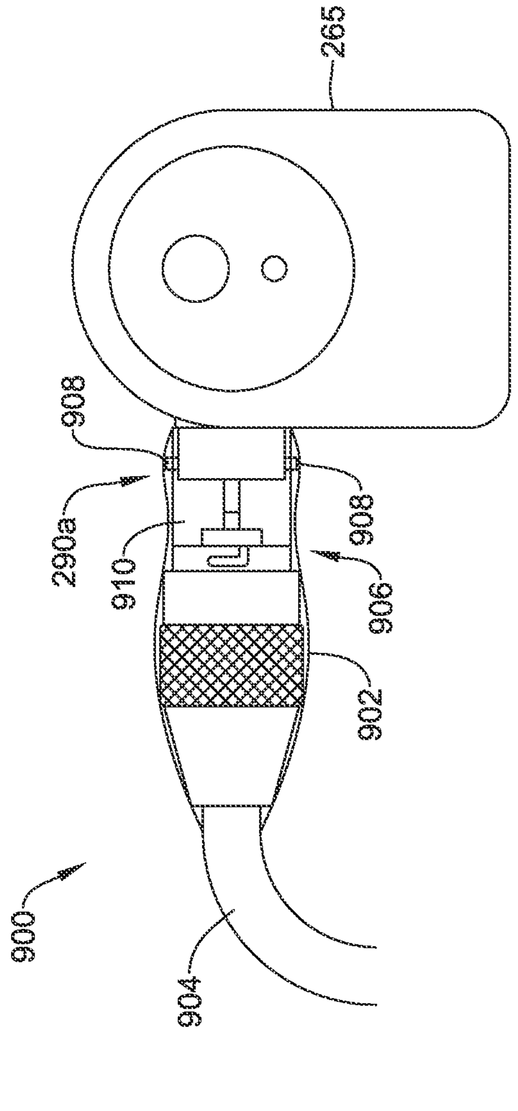
FIG. 9B depicts a side view of the illustrative coupling system of FIG. 9A in a second configuration.

FIG. 9A is a side view of an illustrative coupling system 900 for coupling a tube set 904 having either a male or female connector to a connector portion 265 having either a male or female connector in a first configuration and FIG. 9B is a side view of the illustrative coupling system 900 in a second configuration. In the illustrated embodiment, the tube set 904 includes a receiver 906 having a male configuration and the connector portion 265 includes a first connector type 290*a* having a male configuration. However, the system 900 may be used to connect two female receivers or a male and a female receiver. The coupling system 900 may include a thin, flexible and/or stretchable sleeve 902 such as, but not limited to, silicone, positioned along an outer surface of the tube set 904. In a first configuration, the sleeve 902 may be rolled back on itself to form a tight roll, as shown in FIG. 9A.

When the tube set 904 is to be coupled with the connector portion 265, the receiver 906 is aligned with the first connector 290*a*. The sleeve 902 may then be manually unrolled to extend over the connection between the receiver 906 and the first connector 290*a*, as shown in FIG. 9B. This may create a seal between the receiver 906 and the first connector 290*a* without needing to mechanically mate the receiver 906 and the first connector 290*a*. The sleeve 902 may be long enough to extend completely over the two connectors being coupled. It is contemplated that the flexibility of the sleeve 902 would allow for effective seal creation across connectors that have different diameters, dimensions, geometries, etc. The sleeve 902 may further include a micro- or nanopattern to increase surface area (and grip) of the sleeve 902 to help hold the receivers 906, 290*a* together as effectively as possible in the absence of a mechanical mate. Alternatively, or in addition to adding a pattern, the sleeve 902 could include features such as holes 908 extending through a thickness thereof to specifically fit over existing protrusions in the connectors that would help hold the sleeve 902 in place. In embodiments, the sleeve 902 may rest against an entirety of the outer surfaces of the tube set 904, receiver 906 and first connector 290*a*, along a length of the sleeve 902. In other embodiments, a gap 910 may be present between an inner surface of the sleeve 902 at least some lengths of the tube set 904, receiver 906 and/or first connector 290*a*.

Figure 10A:
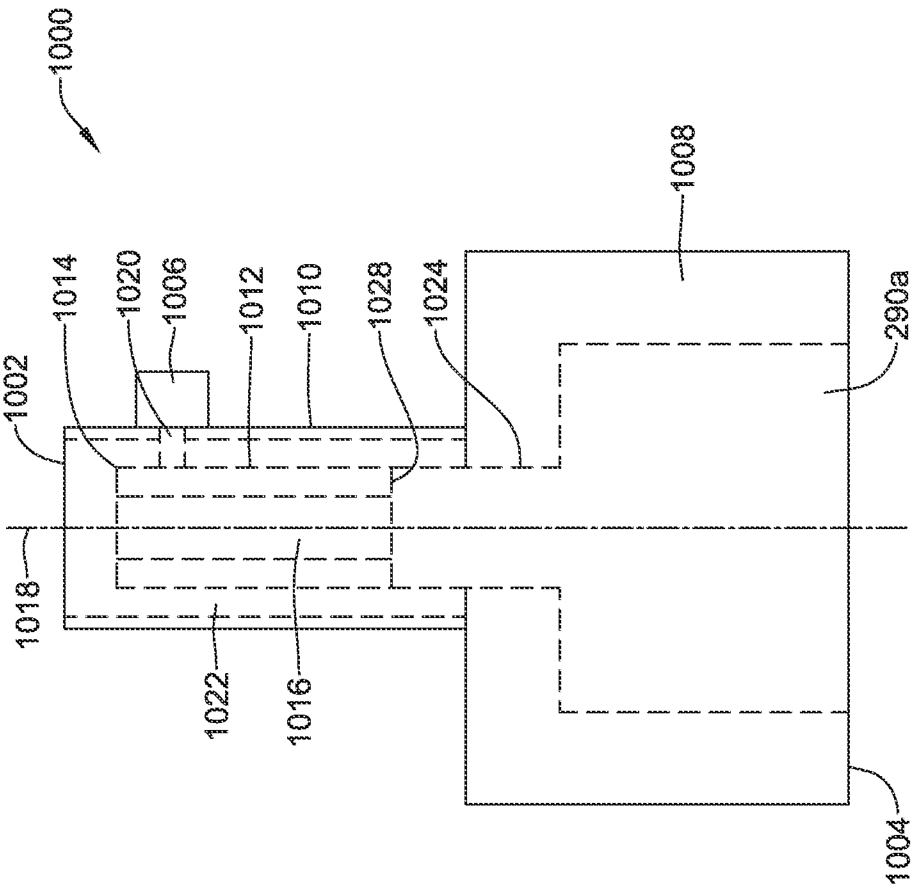
FIG. 10A depicts a side view of an illustrative coupling system for coupling a tube set to a connector portion having either a male or female connector in a first configuration.
Figure 10B:
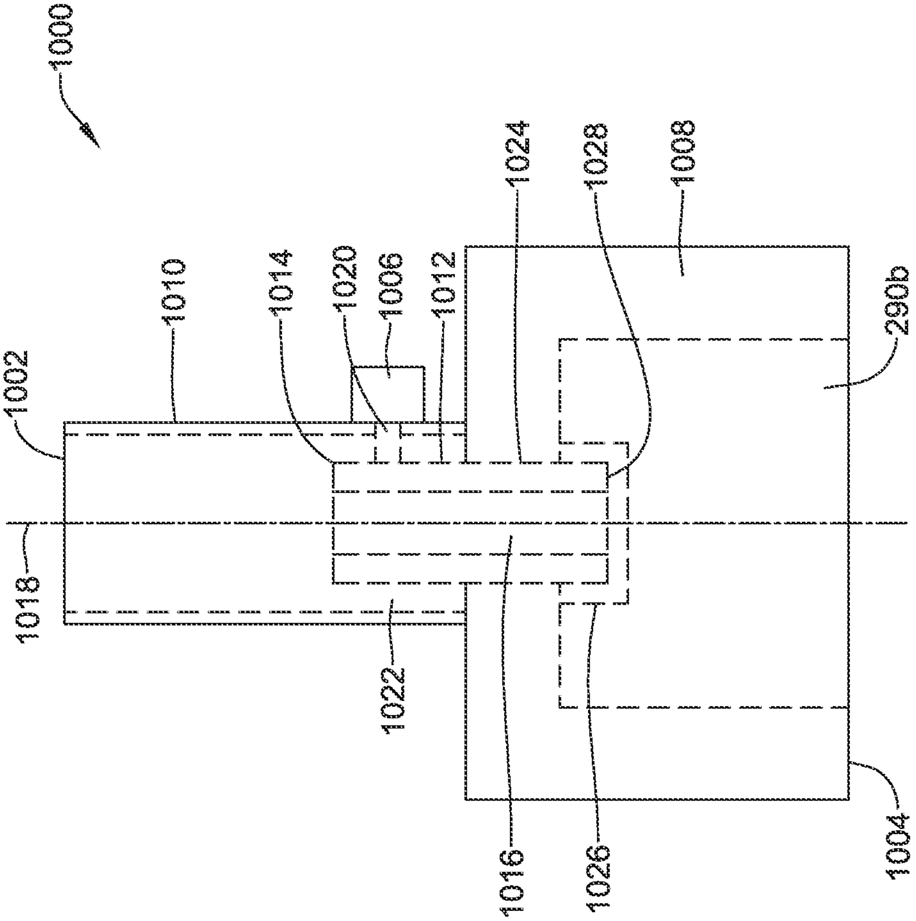
FIG. 10B depicts a side view of the illustrative coupling system of FIG. 10A in a second configuration.

FIGS. 10A and 10B depict schematic side views of another illustrative adaptor 1000 that can couple to either a first connector type 290*a* (e.g., a male receiver 330) or a second connector type 290*b* (e.g. a female receiver 300). The adaptor 1000 extends from a first end 1002 to a second end 1004. The adaptor 1000 may include a housing portion 1008 configured to engage a connector 290 and a neck portion 1010 configured to house an actuatable tube 1012. The actuatable tube 1012 is configured to be fluidly coupled to the lens wash supply tubing 245*c* and defines a lumen 1016 for receiving a flow of fluid therethrough. For example, the lens wash supply tubing 245*c* may be glued, adhered, or otherwise secured to a first end 1014 of the actuatable tube 1012. The gas supply tubing 240*c* may be coupled to the neck portion 1010 adjacent the first end 1002 of the adaptor 1000. The gas supply tubing 240*c* is in fluid communication with an annular lumen 1022 of the neck portion 1010.

A slide actuator 1006 is positioned between the first end 1002 and the second end 1004 exterior to the neck portion 1010. A stem 1020 may extend through a side wall of the neck portion 1010 (e.g., through a longitudinally extending slot). The stem 1020 is coupled to the actuatable tube 1012. The slide actuator 1006 is actuatable to move the actuatable tube 1012 along a longitudinal axis 1018 of the neck portion 1010 to selectively couple the actuatable tube 1012 with a first connector type 290*a* or a second connector type 290*b*. The slide actuator 1006 may include detents or other engagement features configured to mate with corresponding features on the neck portion 1010 to secure slide actuator 1006 in the desired position. The housing portion 1008 may be configured to be disposed over a first connector type 290*a* (FIG. 10A) or a second connector type 290*b* (FIG. 10B). For example, the lumen 1016 of the actuatable tube 1012 may be configured to engage and fluidly couple with a tubular post 1024 of a first connector type 290*a* or an aperture 1026 of the second connector type 290*b*.

The actuatable tube 1012 is movable along the longitudinal axis 1018 to accommodate different connector types 290. For example, when the first connector type (e.g., a male receiver) 290*a* is present on the connector portion 265 of the endoscope system 200, the slide actuator 1006 is moved towards the first end 1002 of the adaptor 1000, as shown in FIG. 10A. This may allow the housing portion 1008 to be disposed over the first connector type 290*a* and the tubular post 1024 to be inserted into the neck portion 1010. The tubular post 1024 may engage the second end 1028 of the actuatable tube 1012 to fluidly couple the lumen 1016 of the actuatable tube 1012 with the tubular post 1024. Air or gas may flow around the exterior of the actuatable tube 1012 through the lumen 1022 of the neck portion 1010 to the gas port on the first connector type 290*a*. The housing portion 1008 may be secured to the first connector type 290*a* with a bayonet style locking mechanism, or other coupling mechanism, such that water/gas supply 245*c*, 240*c* and feed lines 245*b*, 240*b* are in fluid communication.

When the second connector type (e.g., a female receiver) 290*b* is present on the connector portion 265 of the endoscope system 200, the slide actuator 1006 is moved towards the second end 1004 of the adaptor 1000, as shown in FIG. 10B. This may allow the housing portion 1008 to be disposed over the second connector type 290*b* and the actuatable tube 1012 extends into the housing portion 1008 to be inserted into the aperture 1026. The aperture 1026 may engage the second end 1028 of the actuatable tube 1012 to fluidly couple the lumen 1016 of the actuatable tube 1012 with the aperture 1026. Air or gas may flow around the exterior of the actuatable tube 1012 through the lumen 1022 of the neck portion 1010 to the gas port on the second connector type 290*b*. The housing portion 1008 may be secured to the second connector type 290*b* with a bayonet style locking mechanism, or other coupling mechanism, such that water/gas supply 245*c*, 240*c* and feed lines 245*b*, 240*b* are in fluid communication.

As will be appreciated, the lengths of irrigation, lens wash, gas supply, alternate gas supply tubing may have any suitable size (e.g., diameter). In addition, the sizing (e.g., diameters) of the tubing may vary depending on the application. In one non-limiting embodiment, the irrigation supply tubing may have an inner diameter of approximately 6.5 mm and an outer diameter of 9.7 mm. The lens wash supply tubing may have an inner diameter of approximately 5 mm and an outer diameter of 8 mm. The gas supply tubing may have an inner diameter of approximately 2 mm and an outer diameter of 3.5 mm. The alternative gas supply tubing may have an inner diameter of approximately 5 mm and an outer diameter of 8 mm.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

What is claimed is:

1. An adaptor arranged and configured to couple a tube set to an endoscope, the adaptor comprising:

a planar head portion having a first aperture and a second aperture, the first and second apertures extending through a thickness of the planar head portion;

a first floating cylinder extending from a proximal end at least partially disposed within the first aperture of the planar head portion to a distal tip and having a first lumen extending therethrough;

a first O-ring positioned at the distal tip of the first floating cylinder;

a first biasing element disposed about an outer surface of the first floating cylinder and extending from a first end adjacent the first aperture of the planar head portion to a second end proximal to the distal tip of the first floating cylinder;

a second floating cylinder extending from a proximal end at least partially disposed within the second aperture of the planar head portion adjacent the planar head portion to a distal tip and having a second lumen extending therethrough;

a second O-ring positioned at the distal tip of the second floating cylinder; and a second biasing element disposed about an outer surface of the second floating cylinder and extending from a first end adjacent the second aperture of the planar head portion to a second end proximal to the distal tip of the first floating cylinder.

2. The adaptor of claim 1, wherein the first end of the first biasing element is configured to contact a lower surface of the planar head portion adjacent to or within the first aperture thereof and the first end of the second biasing element is configured to contact a lower surface of the planar head portion adjacent to or within the second aperture thereof.

3. The adaptor of claim 1, wherein the first biasing element exerts a distal force on the first floating cylinder.

4. The adaptor of claim 1, wherein the second biasing element exerts a distal force on the second floating cylinder.

5. The adaptor of claim 1, further comprising a first ledge extending radially from an outer surface of the first floating cylinder.

6. The adaptor of claim 5, further comprising a second ledge extending radially from an outer surface of the second floating cylinder.

7. The adaptor of claim 6, wherein the second end of the second biasing element abuts the second ledge.

8. The adaptor of claim 6, wherein the second ledge is proximal to the distal tip of the second floating cylinder.

9. The adaptor of claim 6, wherein the first and second ledges extend about an entire circumference of the first and second floating cylinders.

10. The adaptor of claim 6, wherein the first and second ledges extend about less than an entire perimeter of the first and second floating cylinders.

11. The adaptor of claim 5, wherein the second end of the first biasing element abuts the first ledge.

12. The adaptor of claim 5, wherein the first ledge is proximal to the distal tip of the first floating cylinder.

13. The adaptor of claim 1, wherein the first and second lumens are configured to align with first and second openings in a female connector of an endoscope.

14. The adaptor of claim 1, wherein the first lumen is configured to receive a post defining a first opening of a male connector and the second lumen is configured to align with a second opening of a male connector.

15. The adaptor of claim 1, wherein the proximal ends of the first and second floating cylinders are configured to be coupled with a tube set for use with an endoscopic system and the distal ends of the first and second floating cylinders are configured to be coupled with an air/water connector on an endoscope.

* * * * *